(12) United States Patent
Porteous et al.

(10) Patent No.: US 7,279,305 B1
(45) Date of Patent: Oct. 9, 2007

(54) GENE, DISRUPTED IN SCHIZOPHRENIA

(75) Inventors: David Porteous, Cherry Trees (GB); Kirsty Millar, Central Scotland (GB); Douglas Blackwood, Central Scotland (GB); Walter John Muir, Peebles (GB)

(73) Assignee: N.V. Organon, Oss (NL)

( * ) Notice: Subject to any disclaimer, the term of this patent is extended or adjusted under 35 U.S.C. 154(b) by 613 days.

(21) Appl. No.: 10/148,848

(22) PCT Filed: Nov. 28, 2000

(86) PCT No.: PCT/EP00/11915

§ 371 (c)(1),
(2), (4) Date: Oct. 1, 2002

(87) PCT Pub. No.: WO01/40301

PCT Pub. Date: Jun. 7, 2001

(30) Foreign Application Priority Data

Dec. 1, 1999 (EP) .................................. 99309667

(51) Int. Cl.
C12P 21/06 (2006.01)
C12N 15/00 (2006.01)
C12N 5/00 (2006.01)
C07H 21/02 (2006.01)
C12N 5/02 (2006.01)
C12N 5/06 (2006.01)
C12N 15/09 (2006.01)
C12N 15/63 (2006.01)
C12N 15/70 (2006.01)
C12N 15/74 (2006.01)

(52) U.S. Cl. .................. 435/69.1; 435/320.1; 435/325; 435/363; 536/23.1; 536/23.5

(58) Field of Classification Search .................... None
See application file for complete search history.

(56) References Cited

FOREIGN PATENT DOCUMENTS

| WO | 98 42726 | 10/1998 |
| WO | WO01/40301 | 7/2001 |

OTHER PUBLICATIONS

St. Clair et al., Lancet 336:13-16, 1990.*
Fletcher et al., Am. J. Hum. Genet., Mar. 1993; 52(3):478-90.*
Muir et al., Cytogenet. Cell Gent., 1995; 70(1-2):35-40.*
Evans et al., Genomics Aug. 10, 1995; 28(3):420-428.*
Devon et al., Am. J Med. Genet., Feb. 21, 1997; 74(1):82-90.*
Tandon et al., Eur. J. Neurosci., Aug. 2002; 16(3):403-407.*
Mowry et al., Clin. Exp. Pharmacol. Physiol., Jan.-Feb. 2001; 28(1-2):66-69.*
Vink et al., Biolog. Psych., 2002; 61:53-71.*
TNT T7-coupled reticulocyte lysate system, Promega Co., USA.*
PBluescript II phagemid vectors, Stratagene, USA, Instruction Manual.*
Ohara et al., DNA Res., 4:53-59, 1997.*
T00071 PIR_80 database, Jan. 22, 1999.*
Q9NRI5, UniProt_05.80 database, Feb. 28, 2003.*
Millar et al., Hum. Mol. Genet., 9(9):1415-1423, 2000.*
Tsuang et al., Harvard Rev. Psych., 1999; 7:185-207.*
Hirschorn et al., J. of Clin. Endocrinol. & Metab., 2002; 87(10):4438-41.*
Skolnick et al., Trends in Biotech., 18(1):34-39, 2000.*
Choh, PNAS 77(6):3211-14, 1980.*
Seki N et al: "Characterization of cDNA clones in size-fractionated cDNA libraries from human brain." DNA Research, Oct. 31, 1997, 4 (5) p. 345-349.
-& EMBL Database; Accession No. AB007926, Aug. 13, 1998.
Millar JK et al: "A long-range restriction map across 3 Mb of the chromosome 11 breakpoint region of a translocation linked to schizophrenia: localization of the breakpoint and the search for neighboring genes." Psychiatric Genetics, 1998 Autumn.
Seki, N, et al., "Characterization of cDNA Clones in Size-Fractionated cDNA Libraries from Human Brain", *DNA Research*, 4: 345-349 (1997).
Exhibit 1: GenBank Accession No. AB007926 cited in Seki, N, et al in *DNA Research*, 4: 345-349 (1997) and submitted by Osamu Ohara of Kazusa DNA Research Institute on Oct. 8, 1997.
Hennah et al., "Beyond Schizophrenia: The Role of *DISC1* in Major Mental Illness," Schizophrenia Bulletin, pp. 1-8 (May 12, 2006).
Millar et al., "DISC1 and DISC2; discovering and dissecting molecular mechanisms underlying psychiatric illness," Taylor & Francis, pp. 367-378 (2004).
Kamiya et al., "A schizophrenia-associated mutation of DIScl perturbs cerebral cortex development," Nature Cell Biology, vol. 7, No. 12, pp. 1167-1178 and Supplementary Information pp. 1-4 (Dec. 2005).
Sawa et al., "Two Genes Link Two Distinct Psychoses," Science, vol. 310, pp. 1128-1129 (Nov. 18, 2005).
Millar et al., "DISC1 and PDE4B Are Interacting Genetic Factors in Schizophrenia That Regulate cAMP Signaling," Science, vol. 310, pp. 1187-1191 (Nov. 18, 2005).
Porteous et al., "Disrupted in schizophrenia 1: building brains and memories," Trends in Molecular Medicine, vol. 12, No. 6, pp. 255-261 (Jun. 2006).
Porteous et al., "The Genetics and Biology of Disc1-An Emerging Role in Psychosis and Cognition," Biol Psychiatry, vol. 60, pp. 123-131 (2006).

* cited by examiner

Primary Examiner—Olga N. Chernyshev
(74) Attorney, Agent, or Firm—F. Aaron Dubberley

(57) ABSTRACT

A newly identified gene, DIS1 is disrupted by a (1;11)(q42.1;q14.3) translocation which segregates with schizophrenia. We have examined the genomic structure of DIS1 and found that the gene consists of 13 exons estimated to extend across at least 300 kb of DNA. Exon 11 contains an alternative splice site which removes 66 nucleotides from the open reading frame. The final intron of DIS1 belongs to the rare AT-AC class of introns. 8 expressed sequence tags (ESTs) located within introns 3, 7, 9 and 10 of DIS1 have also been identified. These ESTs have not yet been assigned to DIS1 and may therefore represent further novel genes in the region.

7 Claims, 2 Drawing Sheets

Figure 2:
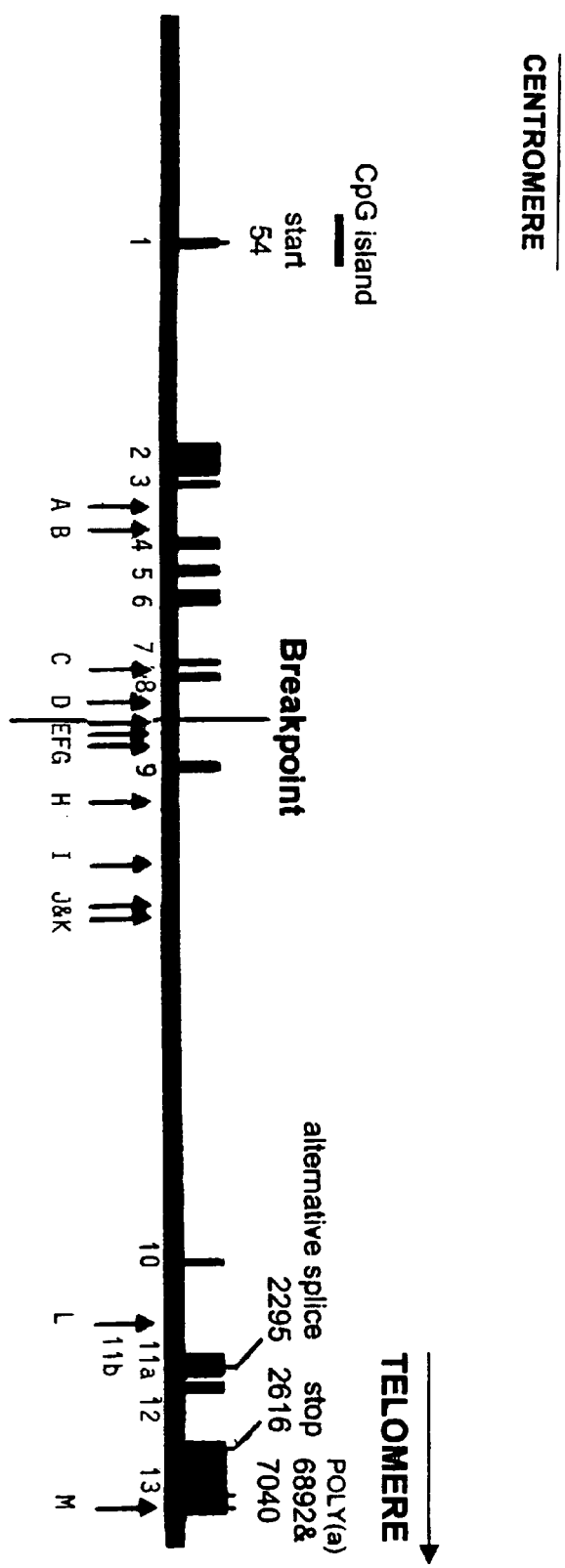

BREAKPOINT wt1  ~ACACGTCATCATCCTGTGAACCATTGAAGT | TGATGGGAGGCAACTTTTCT~ der(11)
SEQ ID NO: 49                      SEQ ID NO: 48 der(1) ~ACACGTCATCATCCTGTGAACCATTGAAGT | TGATGGGAGGCAACTTTTCT~ wt1
SEQ ID NO: 49                       SEQ ID NO: 48 der(11)~ATTTTTAAAATGATACTGAGATATCATGTAAA | TCATTTCTTCCCTCATTATTCA~ wt11
SEQ ID NO: 50                              SEQ ID NO: 52 wt11 ~ATTTTTAAAATGATACTGAGATATCATGTATCAG | TCATTTCTTCCCTCATTATTCA~ der(1)
SEQ ID NO: 51                              SEQ ID NO: 52

Fig. 1

SEQUENCE LISTING

<160> NUMBER OF SEQ ID NOS: 52

<210> SEQ ID NO 1
<211> LENGTH: 7063
<212> TYPE: DNA
<213> ORGANISM: Human

<400> SEQUENCE: 1

```
ggaaggagca ggaggcagcc caggcggagc gggaggagct ggcagcgggg cgcatgccag    60
gcggggtcc tcagggcgcc ccagccgccg ccggcggcgg cggcgtgagc caccgcgcag    120
gcagccggga ttgcttacca cctgcagcgt gctttcggag gcggcggctg gcacggaggc    180
cgggctacat gagaagctcg acagggcctg ggatcgggtt cctttcccca gcagtgggca    240
cactgttccg gttcccagga ggggtgtctg gcgaggagtc ccaccactcg gagtccaggg    300
ccagacagtg tggccttgac tcgagaggcc tcttggtccg gagccctgtt tccaagagtg    360
cagcagcccc tactgtgacc tctgtgagag gaacctcggc gcactttggg attcagctca    420
gaggtggcac cagattgcct gacaggctta gctggccgtg tggccctggg agtgctgggt    480
ggcagcaaga gtttgcagcc atggatagtt ctgagaccct ggacgccagc tgggaggcag    540
cctgcagcga tggagcaagg cgtgtccggg cagcaggctc tctgccatca gcagagttga    600
gtagcaacag ctgcagccct ggctgtggcc ctgaggtccc cccaaccect cctggctctc    660
acagtgcctt tacctcaagc tttagctttta ttcggctctc gcttggctct gccggggaac    720
gtggagaagc agaaggctgc ccaccatcca gagaggctga gtcccattgc cagagccccc    780
aggagatggg agccaaagct gccagcttgg acgggcctca cgaggacccg cgatgtctct    840
ctcagcccctt cagtctcttg gctacacggg tctctgcaga cttggcccag gccgcaagga    900
acagctccag gccagagcgt gacatgcatt ctttaccaga catggacccct ggctcctcca    960
gttctctgga tccctcactg gctggctgtg gtggtgatgg gagcagcggc tcaggggatg   1020
cccactcttg ggacaccctg ctcaggaaat gggagccagt gctgcgggac tgcctgctga   1080
gaaaccggag gcagatggag gtaatatcct taagattaaa acttcagaaa cttcaggaag   1140
atgcagttga gaatgatgat tatgataaag ctgagacgtt acaacaaaga ttagaagacc   1200
tggaacaaga gaaaatcagc ctgcacttttc aacttccttc aaggcagcca gctcttagca   1260
gtttcctggg tcacctggca gcacaagtcc aggctgcctt gcgccgtggg gccactcagc   1320
aggccagcgg agatgacacc cacacccccac tgagaatgga gccgaggctg ttggaaccca   1380
ctgctcagga cagcttgcac gtgtccatca cgagacgaga ctggcttctt caggaaaagc   1440
agcagctaca gaaagaaatc gaagctctcc aagcaaggat gtttgtgctg gaagccaaag   1500
atcaacagct gagaagggaa atagaggagc aagagcagca actccagtgg cagggctgcg   1560
acctgacccc actggtgggc cagctgtccc tgggtcagct gcaggaggtc agcaaggcct   1620
tgcaggacac cctggcctca gccggtcaga ttcccttcca tgcagagcca ccggaaacca   1680
taaggagcct ccaggaaaga ataaaatccc tcaacttgtc acttaaagaa atcactacta   1740
aggtgtgtat gagtgagaaa ttctgcagca ccctgaggaa gaaagttaac gatattgaaa   1800
cccaactacc agccttgctt gaagccaaaa tgcatgccat atcaggaaac catttctgga   1860
```

-continued

```
cggctaaaga cctcaccgag gagattagat cattaacatc agagagagaa gggctggagg    1920
gactcctcag caagctgttg gtgttgagtt ccaggaatgt caaaaagctg ggaagtgtta    1980
aagaagatta caacagactg agaagagaag tggagcacca ggagactgcc tatgaaacaa    2040
gtgtgaagga aaatactatg aagtacatgg aaacacttaa gaataaactg tgcagctgca    2100
agtgtccact gcttgggaaa gtgtgggaag ctgacttgga agcttgtcga ttgcttatcc    2160
agtgcctaca gctccaggaa gccaggggaa gcctgtctgt agaagatgag aggcagatgg    2220
atgacttaga gggagctgct cctcctattc cccccaggct ccactccgag gataaaagga    2280 agacccettt gaaggtattg gaagaatgga agactcacct catcccctct ctgcactgtg    2340
ctggaggtga acagaaagag gaatcttaca tcctttctgc agaacttgga gaaaagtgtg    2400
aagacatagg caagaagcta ttgtacttgg aagatcaact tcacacagca atccacagtc    2460
atgatgaaga tctcattcag tctctcagga gggagctcca gatggtgaag gaaactctgc    2520
aggccatgat cctgcagctc cagccagcaa aggaggcggg agaaagagaa gctgcagctt    2580
cctgcatgac agctggtgtc cacgaagcac aagcctgagg agtgacggga tggggagggg    2640
aggtgggcca ccatgtttgg acccgggggg ctgctcttcc ctcccccgcc atagctaaga    2700
tgcctgaatc aattacggag atacagagcc ttgaggtctt tcagtggaaa ggtggttcat    2760
gttcattctc atcagtgtga aactgaggag tctgcaattt ggaatatgga gagagagact    2820
gatttgctga atttccttct aaatgtcact caaaaatttc ttttccatgt cattcttggg    2880
aatgtcttcc acaggatttg agaatagttt catctcagcc cccattagag agaagttggg    2940
gtgaattctg gaaaaatgtc tcttttcct gtgccatttg ccttctgctg caacgaaaat    3000
atttcctgat tcaagattct ataaaaagga accaagcat aagactctgt catcatacct     3060
gttacacgtt cctacaggtg cacaatctaa gagagctaat taacctcaga gtctggagtt    3120
aacagctttt caccttactt ctcctgtgat ctaatattat cttagaaaaa ttaatatgca    3180
atttccaaaa gatattttgg taagacaaca acctcccagt gatatgccac cttttcaattt   3240 tccttttgtg gcaatgattg catctgaaga aaggatccct gagagtctct gtttcatcag    3300
gacattctga aatttaccca cagtgaggct gtggatggat caggggacct gtataaaatg    3360
tttgagcctg ttccattttc ccgtggaacc tgtttcactc aatgccaggc agtgcagcat    3420
ttaggaaagc agtgcagtac tcagtaaggc agtgcagtac tcagtaacac aatacagtac    3480
tcaggcagtg cagtactcag taagacagtg cagtgctcag taaggcagtg caatactcag    3540
taacagtgta gtactcagta acagtgaagt actcagtaat acagtacagt attcagtaag    3600
gcagtgaagt actcagtaat acaatacagt actcagttag gcagtgcagt actcaggaat    3660
gcagcacagt actcaggcag tgcaatactc agtgcggtac tcagtaacac agtgcagtac    3720
tcagtaacag tgcagtactc agtaacagtg cagtactcag taaggcagtg cagtactcag    3780
taacacagtg cagtactcag taatacagta cagtactcag taaggcagta tggtactcag    3840
taaagcaatg caatgctcag taacacagtg cagtgctcaa taaggcagtg cagtgctcag    3900
taaggcagtg aattgcttag taacacagtg tagtgctcag taggacagca tagtactcag    3960
taacacaggg cagctagtac tcagtactat aagtactgag tacttatata ggcaatgtag    4020
tactcagtaa atcagtgcag tactcagtaa tgcaagggca tttcaggctc ctgctgggct    4080
gcttctttgg cccagctggg actcctattg agacagctgc aaaacaggct gatttcaatt    4140
aggcagcact tccaaagtg cactgaggaa ggtggcccca agagaagctc tctaaacaaa     4200 ggagtacccct ctctggtcaa gtacctttgg taaatacacc ataccataat atctgcttgg   4260
```

-continued

```
agaaccacaa tgcacattag catattagtc tgagagagaa cttatagtaa ggaaactcac    4320
ttgattttat ctaacctcaa actttccaag tttaatggat cgtgaatttt tttcatgtaa    4380
ctcctattca tatcccatag atctagtatt gtacagcact gcattctctg aggaagtccc    4440
agtccaaact ctgatttaca tcactttaga aaccacactc acactttgc agagtgttga     4500 gcttaataac tacctgccac agattggtaa atttaatcca gtggttgttc tgtttgtgct    4560
tctgttctca tttatgtgtt tagggatagt gaggttcctg ccttcactag gatccacgga    4620
tatgagacca ttttttgtcat ttcctgaagt cacactggcg tttccagaag gcatctggtg   4680
ctttgctcag ccttccatgc tgtgcagcac ttctgtcctc agtcaaggag atggccatgc    4740
ttaagccagc aattggctgg ggtccaggaa acaaagcaaa agcacaatat gtgaatgtgc    4800
tgattgtgtt ccctatggct ttatctcgag caaaatacac tctacatatt ttaataataa    4860
gtataattag cttgttcctg gacttcattt tcaatgatga accaaattcc tgaattattt    4920
ataattgtgt ctaaagaaaa ttatgaactg gtcacatggc acttggaatc cttgagttaa    4980
ttccagtgaa gcaaaacttg gaagagtca ggattggcca cattgccaat aacaaattcc     5040
tacttcgaca tatgtctttt caaaaagcct cccagacaca agacatctta accgtcacta    5100
gcccaagtgt tttgtattac tcagacacca tcatgaaata attctgtgag gtcatgatgt    5160
atttgaaaat tctgcaagtt aataactgcc ttgaattgtt tgaacccgaa ataagggttc    5220
tttggtacct ctagtagata gtgtgttcat ttccctgctg caaattttga agtatttggg    5280
caggtgagtc atgttttaac cacaagccat aactcatctg ttgtctttgc ttggtcttag    5340
agtatcattc agaaagtccg ctaagggcca gcgtgcttct tctggctaca caaccttctc    5400
aggacaagcc cactgtctta agccactttg accctgggag acacaggact gtgtatcctc    5460
aatcatacta tacagcagtt tttgtcaggg gaacataaaa atatccaaga gaggttaggg    5520
cttagattta aaagcatcaa aacaacaaca atggaaattt atgttggcga tagccaagac    5580
cacaagcaaa agcacatact ggaaatgatg agttagaatc tgatttgact gggatgtttt    5640
atgagaatgt aagtgtgata ttatactgtc tgccttgctg gaatgctggc tttcaaatgg    5700
tcacccattt ttcttctcact ggcctgagtt aggacatgct atcagtaata gtcccagttc    5760
catccaactt tctgaaattt catttttttt tttgagatgg agtctctctc tgtcacccaa    5820
gttggagtgc agtggcccccg caatctcggc tcactgcaac ctctacctcc caggttcaag   5880
ctattctact gcctcagcct cccaagtagc tggggttaca ggcatttgcc accgggccct    5940
gatgattttt gtatttttag tagagacagg gcttcaccat gttggctagg agggtctcaa    6000
actcctgacc tcaggcgatc cacccccacc tcggcttccc aaagtgctga gattacaggt    6060
gtgagccacc gcacccggcc aactttctga aatttcaaaa ctgaattgat ccttctccaa    6120
attagtatat actattggaa acttgtcttt ccctgcagta aggctggttt ccccaccccca   6180 gaaacatgta acggttggta ccatgctaag cccttgccat gctaagccct ttacagtcat    6240
atcctataat ccccatatca accttataag gaaggtgttt gtagatgatg caactgagcc    6300
ttaagaggac taattccctt tttctaaggc acagagctgg taaaatgtga agtaatagtg    6360
aacctaacag tcagagacag gcagcatgct cttaactagt gctcttccta aagttccttt    6420
aatgtccttt tgagattttg agccatggaa cttacttgtt cacctggcta agaactcatg    6480
gccactgtgg aaatcttggt tagggagtca aagaaactga gcctggggca aacgaggctt    6540
cccacactgc caggggagcc tcactgtgaa gtctaggctc agacaggcat caacaaacct    6600
```

-continued

```
attcacccca ccatcatcct gatctaacca ttccccagtc atcccaggaa aaccactcac   6660
agcctgacac tgggctgact ttcttgaaga tcctcatcca attggtgttt ttcagaagtg   6720
ttccaatatt atgaattctg tgttgtggag aaaagcaacc atgcatttac tggtcaatgc   6780
cttcttgtat atgtaattca atacttttac ttttaatatc ctcaccttat ctaatctttg   6840
aattttgtca tgtaatttat tgcttcatta aggttacttt tgttatacaa aataaaagc    6900 tgatatccaa ggcatggtgc atcttgatga ttttttgtcc tttgaagtat ggatgataga   6960
aaaatgtatc aggtttattc atctcatctt tctgttacag gatgattaat tgtacagtta   7020
catcacatga aacatttata ataaagtcat gctttagaat tgc                      7063
```

<210> SEQ ID NO 2
<211> LENGTH: 854
<212> TYPE: PRT
<213> ORGANISM: Human

<400> SEQUENCE: 2

```
Met Pro Gly Gly Gly Pro Gln Gly Ala Pro Ala Ala Gly Gly Gly
 1               5                  10                  15

Gly Val Ser His Arg Ala Gly Ser Arg Asp Cys Leu Pro Ala Ala
                20                  25                  30

Cys Phe Arg Arg Arg Leu Ala Arg Arg Pro Gly Tyr Met Arg Ser
                35                  40                  45

Ser Thr Gly Pro Gly Ile Gly Phe Leu Ser Pro Ala Val Gly Thr Leu
                50                  55                  60

Phe Arg Phe Pro Gly Gly Val Ser Gly Glu Glu Ser His His Ser Glu
65                  70                  75                  80

Ser Arg Ala Arg Gln Cys Gly Leu Asp Ser Arg Gly Leu Leu Val Arg
                85                  90                  95

Ser Pro Val Ser Lys Ser Ala Ala Pro Thr Val Thr Ser Val Arg
                100                 105                 110

Gly Thr Ser Ala His Phe Gly Ile Gln Leu Arg Gly Thr Arg Leu
                115                 120                 125

Pro Asp Arg Leu Ser Trp Pro Cys Gly Pro Gly Ser Ala Gly Trp Gln
                130                 135                 140

Gln Glu Phe Ala Ala Met Asp Ser Ser Glu Thr Leu Asp Ala Ser Trp
145                 150                 155                 160

Glu Ala Ala Cys Ser Asp Gly Ala Arg Arg Val Arg Ala Ala Gly Ser
                165                 170                 175

Leu Pro Ser Ala Glu Leu Ser Ser Asn Ser Cys Ser Pro Gly Cys Gly
                180                 185                 190

Pro Glu Val Pro Pro Thr Pro Pro Gly Ser His Ser Ala Phe Thr Ser
                195                 200                 205

Ser Phe Ser Phe Ile Arg Leu Ser Leu Gly Ser Ala Gly Glu Arg Gly
                210                 215                 220

Glu Ala Glu Gly Cys Pro Pro Ser Arg Glu Ala Glu Ser His Cys Gln
225                 230                 235                 240

Ser Pro Gln Glu Met Gly Ala Lys Ala Ala Ser Leu Asp Gly Pro His
                245                 250                 255

Glu Asp Pro Arg Cys Leu Ser Gln Pro Phe Ser Leu Leu Ala Thr Arg
                260                 265                 270

Val Ser Ala Asp Leu Ala Gln Ala Ala Arg Asn Ser Ser Arg Pro Glu
                275                 280                 285

Arg Asp Met His Ser Leu Pro Pro Met Asp Pro Gly Ser Ser Ser Ser
```

-continued

```
          290                 295                 300
Leu Asp Pro Ser Leu Ala Gly Cys Gly Gly Asp Gly Ser Ser Gly Ser
305                 310                 315                 320

Gly Asp Ala His Ser Trp Asp Thr Leu Leu Arg Lys Trp Phe Pro Val
                325                 330                 335

Leu Arg Asp Cys Leu Leu Arg Asn Arg Arg Gln Met Glu Val Ile Ser
                340                 345                 350

Leu Arg Leu Lys Leu Gln Lys Leu Gln Glu Asp Ala Val Glu Asn Asp
                355                 360                 365

Asp Tyr Asp Lys Ala Glu Thr Leu Gln Gln Arg Leu Glu Asp Leu Glu
370                 375                 380

Gln Glu Lys Ile Ser Leu His Phe Gln Leu Pro Ser Arg Gln Pro Ala
385                 390                 395                 400

Leu Ser Ser Phe Leu Gly His Leu Ala Ala Gln Val Gln Ala Ala Leu
                405                 410                 415

Arg Arg Gly Ala Thr Gln Gln Ala Ser Gly Asp Asp Thr His Thr Pro
                420                 425                 430

Leu Arg Met Glu Pro Arg Leu Leu Glu Pro Thr Ala Gln Asp Ser Leu
                435                 440                 445

His Val Ser Ile Thr Arg Arg Asp Trp Leu Leu Gln Glu Lys Gln Gln
                450                 455                 460

Leu Gln Lys Glu Ile Glu Ala Leu Gln Ala Arg Met Phe Val Leu Glu
465                 470                 475                 480

Ala Lys Asp Gln Gln Leu Arg Arg Glu Ile Glu Glu Gln Glu Gln Gln
                485                 490                 495

Leu Gln Trp Gln Gly Cys Asp Leu Thr Pro Leu Val Gly Gln Leu Ser
                500                 505                 510

Leu Gly Gln Leu Gln Glu Val Ser Lys Ala Leu Gln Asp Thr Leu Ala
                515                 520                 525

Ser Ala Gly Gln Ile Pro Phe His Ala Glu Pro Pro Glu Thr Ile Arg
                530                 535                 540

Ser Leu Gln Gln Arg Ile Lys Ser Leu Asn Leu Ser Leu Lys Glu Ile
545                 550                 555                 560

Thr Thr Lys Val Cys Met Ser Glu Lys Phe Cys Ser Thr Leu Arg Lys
                565                 570                 575

Lys Val Asn Asp Ile Glu Thr Gln Leu Pro Ala Leu Leu Glu Ala Lys
                580                 585                 590

Met His Ala Ile Ser Gly Asn His Phe Trp Thr Ala Lys Asp Leu Thr
                595                 600                 605

Glu Glu Ile Arg Ser Leu Thr Ser Glu Arg Glu Gly Leu Glu Gly Leu
610                 615                 620

Leu Ser Lys Leu Leu Val Leu Ser Ser Arg Asn Val Lys Lys Leu Gly
625                 630                 635                 640

Ser Val Lys Glu Asp Tyr Asn Arg Leu Arg Arg Glu Val Glu His Gln
                645                 650                 655

Glu Thr Ala Tyr Glu Thr Ser Val Lys Glu Asn Thr Met Lys Tyr Met
                660                 665                 670

Glu Thr Leu Lys Asn Lys Leu Cys Ser Cys Lys Cys Pro Leu Leu Gly
                675                 680                 685

Lys Val Asn Glu Ala Asp Leu Glu Ala Cys Arg Leu Leu Ile Gln Cys
                690                 695                 700

Leu Gln Leu Gln Glu Ala Arg Gly Ser Leu Ser Val Glu Asp Glu Arg
705                 710                 715                 720
```

```
Gln Met Asp Asp Leu Glu Gly Ala Ala Pro Ile Pro Pro Arg Leu
            725                 730                 735

His Ser Glu Asp Lys Arg Lys Thr Pro Leu Lys Val Leu Glu Glu Trp
            740                 745                 750

Lys Thr His Leu Ile Pro Ser Leu His Cys Ala Gly Gly Glu Gln Lys
            755                 760                 765

Glu Glu Ser Tyr Ile Leu Ser Ala Glu Leu Gly Glu Lys Cys Glu Asp
        770                 775                 780

Ile Gly Lys Lys Leu Leu Tyr Leu Glu Asp Gln Leu His Thr Ala Ile
785                 790                 795                 800

His Ser His Asp Glu Asp Leu Ile Gln Ser Leu Arg Arg Glu Leu Gln
            805                 810                 815

Met Val Lys Glu Thr Leu Gln Ala Met Ile Leu Gln Leu Gln Pro Ala
            820                 825                 830

Lys Glu Ala Gly Glu Arg Glu Ala Ala Ser Cys Met Thr Ala Gly
            835                 840                 845

Val His Glu Ala Gln Ala
    850

<210> SEQ ID NO 3
<211> LENGTH: 832
<212> TYPE: PRT
<213> ORGANISM: Human

<400> SEQUENCE: 3

Met Pro Gly Gly Gly Pro Gln Gly Ala Pro Ala Ala Gly Gly Gly
1               5                   10                  15

Gly Val Ser His Arg Ala Gly Ser Arg Asp Cys Leu Pro Pro Ala Ala
            20                  25                  30

Cys Phe Arg Arg Arg Leu Ala Arg Arg Pro Gly Tyr Met Arg Ser
            35                  40                  45

Ser Thr Gly Pro Gly Ile Gly Phe Leu Ser Pro Ala Val Gly Thr Leu
    50                  55                  60

Phe Arg Phe Pro Gly Gly Val Ser Gly Glu Ser His His Ser Glu
65                  70                  75                  80

Ser Arg Ala Arg Gln Cys Gly Leu Asp Ser Arg Gly Leu Leu Val Arg
                85                  90                  95

Ser Pro Val Ser Lys Ser Ala Ala Pro Thr Val Thr Ser Val Arg
            100                 105                 110

Gly Thr Ser Ala His Phe Gly Ile Gln Leu Arg Gly Thr Arg Leu
            115                 120                 125

Pro Asp Arg Leu Ser Trp Pro Cys Gly Pro Gly Ser Ala Gly Trp Gln
    130                 135                 140

Gln Glu Phe Ala Ala Met Asp Ser Ser Glu Thr Leu Asp Ala Ser Trp
145                 150                 155                 160

Glu Ala Ala Cys Ser Asp Gly Ala Arg Val Arg Ala Ala Gly Ser
                165                 170                 175

Leu Pro Ser Ala Glu Leu Ser Ser Asn Ser Cys Ser Pro Gly Cys Gly
            180                 185                 190

Pro Glu Val Pro Pro Thr Pro Gly Ser His Ser Ala Phe Thr Ser
            195                 200                 205

Ser Phe Ser Phe Ile Arg Leu Ser Leu Gly Ser Ala Gly Glu Arg Gly
    210                 215                 220

Glu Ala Glu Gly Cys Pro Pro Ser Arg Glu Ala Glu Ser His Cys Gln
```

-continued

```
            225                 230                 235                 240

Ser Pro Gln Glu Met Gly Ala Lys Ala Ala Ser Leu Asp Gly Pro His
                245                 250                 255

Glu Asp Pro Arg Cys Leu Ser Gln Pro Phe Ser Leu Leu Ala Thr Arg
                260                 265                 270

Val Ser Ala Asp Leu Ala Gln Ala Ala Arg Asn Ser Ser Arg Pro Glu
                275                 280                 285

Arg Asp Met His Ser Leu Pro Asp Met Asp Pro Gly Ser Ser Ser Ser
                290                 295                 300

Leu Asp Pro Ser Leu Ala Gly Cys Gly Gly Asp Gly Ser Ser Gly Ser
305                 310                 315                 320

Gly Asp Ala His Ser Trp Asp Thr Leu Leu Arg Lys Trp Glu Pro Val
                    325                 330                 335

Leu Arg Asp Cys Leu Leu Arg Asn Arg Arg Gln Met Glu Val Ile Ser
                340                 345                 350

Leu Arg Leu Lys Leu Gln Lys Leu Gln Glu Asp Ala Val Glu Asn Asp
            355                 360                 365

Asp Tyr Asp Lys Ala Glu Thr Leu Gln Gln Arg Leu Glu Asp Leu Glu
        370                 375                 380

Gln Glu Lys Ile Ser Leu His Phe Gln Leu Pro Ser Arg Gln Pro Ala
385                 390                 395                 400

Leu Ser Ser Phe Leu Gly His Leu Ala Ala Gln Val Gln Ala Ala Leu
                405                 410                 415

Arg Arg Gly Ala Thr Gln Gln Ala Ser Gly Asp Asp Thr His Thr Pro
                420                 425                 430

Leu Arg Met Glu Pro Arg Leu Leu Glu Pro Thr Ala Gln Asp Ser Leu
                435                 440                 445

His Val Ser Ile Thr Arg Arg Asp Trp Leu Leu Gln Glu Lys Gln Gln
            450                 455                 460

Leu Gln Lys Glu Ile Glu Ala Leu Gln Ala Arg Met Phe Val Leu Glu
465                 470                 475                 480

Ala Lys Asp Gln Gln Leu Arg Arg Glu Ile Glu Glu Gln Glu Gln Gln
                485                 490                 495

Leu Gln Trp Gln Gly Cys Asp Leu Thr Pro Leu Val Gly Gln Leu Ser
                500                 505                 510

Leu Gly Gln Leu Gln Glu Val Ser Lys Ala Leu Gln Asp Thr Leu Ala
            515                 520                 525

Ser Ala Gly Gln Ile Pro Phe His Ala Glu Pro Pro Glu Thr Ile Arg
        530                 535                 540

Ser Leu Gln Glu Arg Ile Lys Ser Leu Asn Leu Ser Leu Lys Glu Ile
545                 550                 555                 560

Thr Thr Lys Val Cys Met Ser Glu Lys Phe Cys Ser Thr Leu Arg Lys
                565                 570                 575

Lys Val Asn Asp Ile Glu Thr Gln Leu Pro Ala Leu Leu Glu Ala Lys
                580                 585                 590

Met His Ala Ile Ser Gly Asn His Phe Trp Thr Ala Lys Asp Leu Thr
                595                 600                 605

Glu Glu Ile Arg Ser Leu Thr Ser Glu Arg Glu Gly Leu Glu Gly Leu
            610                 615                 620

Leu Ser Lys Leu Leu Val Leu Ser Ser Arg Asn Val Lys Lys Leu Gly
625                 630                 635                 640

Ser Val Lys Glu Asp Tyr Asn Arg Leu Arg Arg Glu Val Glu His Gln
                645                 650                 655
```

-continued

```
Glu Thr Ala Tyr Glu Thr Ser Val Lys Glu Asn Thr Met Lys Tyr Met
            660                 665                 670

Glu Thr Leu Lys Asn Lys Leu Cys Ser Cys Lys Cys Pro Leu Leu Gly
        675                 680                 685

Lys Val Trp Glu Ala Asp Leu Glu Ala Cys Arg Leu Leu Ile Gln Cys
    690                 695                 700

Leu Gln Leu Gln Glu Ala Arg Gly Ser Leu Ser Val Glu Asp Glu Arg
705                 710                 715                 720

Gln Met Asp Asp Leu Glu Gly Ala Ala Pro Ile Pro Pro Arg Leu
            725                 730                 735

His Ser Glu Asp Lys Arg Lys Thr Pro Leu Lys Glu Ser Tyr Ile Leu
        740                 745                 750

Ser Ala Glu Leu Gly Glu Lys Cys Glu Asp Ile Gly Lys Lys Leu Leu
    755                 760                 765

Tyr Leu Glu Asp Gln Leu His Thr Ala Ile His Ser His Asp Glu Asp
770                 775                 780

Leu Ile Gln Ser Leu Arg Arg Glu Leu Gln Met Val Lys Glu Thr Leu
785                 790                 795                 800

Gln Ala Met Ile Leu Gln Leu Gln Pro Ala Lys Glu Ala Gly Glu Arg
            805                 810                 815

Glu Ala Ala Ala Ser Cys Met Thr Ala Gly Val His Glu Ala Gln Ala
        820                 825                 830
```

<210> SEQ ID NO 4
<211> LENGTH: 33780
<212> TYPE: DNA
<213> ORGANISM: Human
<220> FEATURE:
<221> NAME/KEY: misc_feature
<222> LOCATION: (2830)..(2830)
<223> OTHER INFORMATION: n = A, G, C or T
<220> FEATURE:
<221> NAME/KEY: misc_feature
<222> LOCATION: (2909)..(2909)
<223> OTHER INFORMATION: n = A, G, C or T
<220> FEATURE:
<221> NAME/KEY: misc_feature
<222> LOCATION: (2927)..(2927)
<223> OTHER INFORMATION: n = A, G, C or T
<220> FEATURE:
<221> NAME/KEY: misc_feature
<222> LOCATION: (8433)..(8610)
<223> OTHER INFORMATION: n = A, G, C or T
<220> FEATURE:
<221> NAME/KEY: misc_feature
<222> LOCATION: (21550)..(21550)
<223> OTHER INFORMATION: n = A, G, C or T

<400> SEQUENCE: 4

```
ttcctgacat tccgggtgc gggacggcgt taccagaaac tcagaaggtt cgtccaacca     60
aaccgactct gacggcagtt tacgaagaga gatgatagg  tctgcttcag taagccagat   120
gctacacaat taggcttgta catattgtcg ttagaacgcg gctacaatta atacataacc   180
ttatgtatca tacacatacg atttaggtga cactatagaa tactaggatc ttccctccac   240
atgtgtctgt ctccgcatct cttcttttct tttctttttct ttttttttc aagatacagt   300 ctccctctgt cgcccaggct ggagtgcagt ggcatgatat cggctcactg caagctctgc   360
ctcccgggtt cacgccattc tcctgcctca gcctcccaag tagctgggac tacaggcgcc   420
tgccaccacg ctcggctaat ttttgtatt  tttagtagag acggggtttc accgtgttag   480
ccaggatggt ctccatctcc tgaccttgtg atctgcccac ctcggcctcc caaagtgctg   540
```

-continued

```
ggattacagg cgtgagccac cgcgcctggc cttccacatc tctccttata atgataccag      600
tcatattgga ttggggttca ccctaatgac tttattttaa atttattacc tattgaaaag      660
ccctatctcc aaacatcgtc acattcttag gtactggggg attccggact ccaacctgtg      720
aattttgggg gacacaactc aaccggtgac aggcaccttt gcatttaatt ttcttttgcc      780
acagccaccc cccaggctca tctgctgctg atgtgcgttc tgtgcagcac attcatgtca      840
gtagtctcaa tttttgtaag gtttcatttg ttgagggtga aatttggtca tatgattgga      900
acaccagttt gtgagtaaag aataatgtgt atttacaaat catgatattg attatattgt      960
acattgaaca aaattctgaa atagaattcc aaaaatttgt ctggatgaca gttcatttta     1020
aataggtaca cagcttctgg gagcggtagt tagtattgtt caatagttag gagagcagat     1080
agttagactg cctgggttac tgtttaatct cccataatta ccagctggtt acccctggga     1140
aagttactta aacctctctt agtctctttg atgaaatttt cttgtcttac aatgtagata     1200
attagagttt ctacttcata gagttataat aagaatttaa aatgctcatc tacatagaga     1260
atttgggaga gtgtctggta catagtaagt gttcaataaa tgttggattc tattatttcc     1320
agggcagcca ctttgaatga agatactcat ttgggtaaat taggtctggt gtgtttctga     1380
aaatgtgttc gctaatttgt ttggacaaat tgtgtgtttc tagggtaagg cataatttca     1440
tctgagagga taattcttgt ttgttatgaa taatatgcaa gttttttaaa aagtggggat     1500
tggtttcact cattaaagta cacggaactc ctgcttgtca gcattgaact ggtcttattt     1560
tctggttttt ggtttgtagt cctgctcctg gaattacggt ttggggacca cagtgtgatg     1620
gcagcagcaa catgtgtgta tgtttggggg actaatgtga catctttgta ccctaggcca     1680
gacacccac ttcaataaaa gcagattccc tgttatcttt attatgtttt atagtgctgt     1740
gtaaactttg gtttgagaga attcttctac tataaatagc ctgaaaccca ctagcatagt     1800
atatagattc ctcatatcgt ctgctccccc aacaattgct tttattctgt atataccccca    1860
gggatacaac taatgttaat agtagcctga gcaaaacgta attgggaagg caaatctgtt     1920
gcaaaaagga atatagcata aattaattat aaatcaaatt aaatataaaa caatgcattt     1980
aattatctgc atcactgccc ccttcctcta acatggatat ctgagaggag actgattttc     2040
tttctgggat agggccagat ctcagcccag acaagtgaac tgtgtcaacc cctgaaaga    2100
tggtgcttga cctcctttt tgtgatatgt tgggcattag ctaaaggcac tgctgttttg     2160
gtcagctaaa atttcagtat cagtaagagg atctactacc tatctgaatt gttaatgcat     2220
gggctagtct ttgtgtgtga ttgggaacac ctacttataa tatactatta aatgctcata     2280
taggttcaat gatgtgttga accatttatt aaaaatgtat ttgttgaatg gactctaacg     2340
agcccagcaa gggaaagtgc atttctgccc aaggaaggtt ttcagtttgg gcagcaggca     2400
ttagccaccc aaagctggtg ctgctgttag aatcagagga agaaccagta cgggtccatg     2460
ttggatgccc tctgtccttc tcaccaccct aagtggtttc atctgcccca atctccatgt     2520
ctgtgtgaca ctctgactta tgttctctca aagatccaa tccctggcca gccagagtct     2580
agcattctcc aggcaggatt ccaaacattg ttttccactg ttcccactga gtacacgaat     2640
ttttgtcaga tggcagctcc tgaattctga agagtctggt gtcacatgcc ccacctctgt     2700
caaacctcac ttcttccatt tgggctgatc tcagctggac tggaaaaccc tcctctgttg     2760
aaagtaggtc taaagtggta atgactgatt agtacggacc tgcaccagtt cccaggtatt     2820
tacaattgan acgagtttgc ttatactcag aagtgacaaa atggtggatg tgataacatc     2880
```

```
aaaatatagt tcttacagtt gaagaacana caaacaaaaa tcagcanatt ggcagcttag    2940
ctccaatact tggcaacctc tggtatgaga tttcctgaca ccctgcacac tttcccttcc    3000
ctcccaacac ataccccaga acccttgacc tttccttttg caggtcatca tttaatcaag    3060
taatcactcc tcttctagca tctgttacat tttctggcat ttctagcagc agtaagtggt    3120
tgagggcagg aaccatgtct tcatgctcta agttcctagc ttgctgggtg cccagtagat    3180
agatatttga agaatgagtg agttcatgaa tgcatgaaag agtggaaaac tctagaatgg    3240
atgttctcac tgctgtgagc atccacgtaa tccagtcctg ttcttccctc cccttctga    3300 cctctatcac tctgcgggc ccatggaccc catgacgggc ttacactgct gaagaggcct    3360
gtctggtttt gtcacattca gactttcttc ctccaaatca tctctcatag tgccgcccaa    3420
ttatttttct aaaaacaaa aacacttctt tcatattgct ctcttgctag aaaacggaat    3480
gatttctcat tgcttgaggg ataaaactca aaactcctta gtctggcatt taatactgac    3540
tagagcttgc ccttgatatt tctttaaaaa tattttaatt gtaaatattt caaacatatt    3600
taaaaataca acactcattt atccactact aggattaaac aaatagtaga atttacccca    3660
tatttacttt gatttcttt ccctgactaa ataaatttat tttattttat ttttggaga    3720 tggagtcagg gtttcaccat gttggccacg ctgctcgcga actcctgact tcaggtgatc    3780 cacccccaa ggcctcccaa agtgctggaa ttacaggcgt gagccaccac ggcccggccc    3840
ctaactaact aaataagcaa ccattataga tacagatagg ccccacccca tccttctctc    3900
tcttttccta ccagaaatag tcatttccct gtttatcttt cacaactcac ctgtgagaac    3960
catttagtcc agttagattt atcttcttgc tagaatttca ttctcttttt tttttccctt    4020
tgaggcccag ttcacttttc acctcttctg gtaagctttc ccaccaatct cctagttcta    4080
aattgctgca caagttattt tctccattgc tcaaggcaga caatattctg cctggtgaca    4140
gcttttatgt agcagttttc tcctagtatt gattttctat tccccttata gtaatttttt    4200
cctcttgctt tatattatag cgaattgcat gcctgtgttt cttctctact aggtaacaac    4260
cttcagaata agatctgact cttaattgca ttgattcatt cattctacag gtattgactg    4320
agggcttact aacaagctcc aggaattctt taagcactgg ggatgcagga gtggacacaa    4380
cagacagtcg ctgccttcat ggaacttaag ttccagtggg agagagagaa attacatgaa    4440
taaataaata tgtcaagatg aaaagtgcta cggagaaaag agaagcagga gaaggctaag    4500
ggggtgctat ctcagacata ctttaaatat gtgtctctcc tttatgctct atgtcaatgc    4560
cgaatgcaga gggctctggg tacatatttg ctgaattgca ttgtctaccc aaatagatac    4620
tatttgattc cctgctggtg agacactact cagtgtagac cttccttctg ggaaggttgt    4680
tataggaatg cagattttaa tcctttgctg ccaggagcac accttggctg ttcttcccgt    4740
tatcagtaga tgtacactct ggcatgata aaattgtaat actagcttta gtaaggcata    4800 ataagggag aaaggtctgt ttcctagcac catatttatt ccgtagtcaa atggagccaa    4860
tttggcatca tctttcctcc tgcacttctt cgtccatcag accagtggaa ggttcacttt    4920
ttgcagtgtt cctaactgta gtggtattga attgtggtta ccaagaagac caatctcctc    4980
tttttaattc ttccagcctc caggaaagaa taaaatccct caacttgtca cttaaagaaa    5040
tcactactaa gtaagtacc tttatattcc cattttccaa agaagcctat gaagttttcg    5100
tttgacttga ttttacatct agatcttagg atacctggct tctgcaaaaa aagatgtaga    5160
ctttgtcaag ccattttgca ggcccaatga tgagttaaaa gagccaggag agagtgcttc    5220
tgtcatagtg gaggtcttga cttgtggaca ccccagaaat ggactggttt ggcctttgct    5280
```

```
acaaaaggag ctgtcaattt agggactgaa aaaggactgc cactatgcat attgaaagcc    5340
tttgcttaaa gatgcattcg gggcttggtg cggtggctca cgcctgtaat cccagcactt    5400
tgggaggccg aggtgggtgg atcacctgag gtcagaagtt tgagaccagc ctgaccaaca    5460
ttgtgaaacc ccgtctctcc tgaaaataca aaaattagct gggtgtggtg gagggtgcct    5520
gtaatcccag ctactcagga ggctgaggta ggagaattgc tttaacccag gtggttgagg    5580
ttgcagtgag ccgagattgc accattgcat tccagcctgg gagacagagc gagactctat    5640
ctcaaagaaa aaaaaaatgc tttcaggatg gtagtaattt gagaaattaa ttactttct    5700 tcccaggagg gcaatgtctg gtttcctcac aaatagaaca gttggtgact gttttttgt    5760 tctttaaagc ttttcagttg gcttgacaat cattttgcct actttatcca tcgtttatac    5820
tgccatagca agaccttggt ttgtgtacag acagaatacg tcttcactat tccctgagag    5880
cacagtcaat taaatagtca atgtcctcat tagttaggat aaccacagtt tacaaaacaa    5940
aagcccttct catatgtatt tatacctggc caagttattg acagactgag aaacaggatc    6000
aattactctg tgaattatga ctaaatgttg tggcagagaa ctgggtatga atcattcatt    6060
atttgcagtt ggtctgggaa cgaggggtgg ttgtaccatg gtcgaaatgt aaaaaggaca    6120
gcttgctgag cagagagcaa cgcagctgag agcctgttgg cctggaagga ctctcttccg    6180
gtctctgtgc ccagagaaag aaagtcttgg accctagatc aggaaacacg ccaagggatc    6240
accgcagcta agccagaatc agggatgtga tgttggcaaa aatgtctgga gttactctgt    6300
gcattttctc catttctgta tctaatttat ttctgaaaac aacacccagt gattttgcta    6360
aaggtcacag agccgcaggt ttgatgggta attataactt gtgtacaaag agagcttcct    6420
gttaggaaca agtggtgccc gtaagacagc atcggagcca gggacccaga aatgcttgac    6480
ttctgctctg ctcacccaaa ggttctttca cccaggctgg agtgtaatgg catgatcata    6540
gctcactcag ccttgatctc ccgggctcag gtaatcctcc tgcctcagcc tcccaagtag    6600
ctgggactac agacacatgc taccttgccc agctaaattt gtttgatttt cagtagagac    6660
caggtcttgc taggttgccc aggctggtct tgaacttctg agctcaagcg atcctcctgc    6720
ctcagtgtgt caaaattggg attgcaggca agagccaccg cacctgcctc tcttacattt    6780
tctgctgttt atcaggtgcg tcctgatttc tatgtagaat taaagatggg gaggactgtc    6840
ttgggtctga gtttattgac tatcttcaga acatactgta tgggtaatat gaatgcatct    6900
gtacaccaac gttgaggata caggtgtgcc tattatataa tgcagatggt gcttatatgg    6960
gtgtgtgtat gacactgtat attgtggata cacacatata ctgatacgca cccaatatta    7020
ggatttgctg aaaatttcca actactatta aagatcttag attttcccaa atatcaaaaa    7080
tgggttgttt tgtttgcata cagtcctact ccatttgagt tgctataaca aagtactgta    7140
gacgaggtgg cttataaaca acagaaattt aattcccatc actttgaagc ctggaagtct    7200
gggattaggg ttccagcatg gctaagttct ggtgagaggc cctcttacag gctgcagacg    7260
gttgacttct tgttgtattc ctgcatggaa gaaagagggc aaggcggggt ctctgggggct    7320 tctttataag ggtactaatc cccttcatgg gggcccacc ttcatgacct gatcacctcc    7380
caaaggcccc acctcctaat gccatcacct tgggagttag actttcaacc tatgaattct    7440
gggggggaaa aaacatctcc aaccattgca catacccttct ctaatacatt tataaaactt    7500
tataattact tcgcttttcc ataaaattaa ggaactcaca tctttgattt taaaatgtaa    7560
acataaaagc cccatttgat aatgagttcc ttggtgtcca atttttatttg taaataaaaa    7620
```

-continued

```
ggatacacag gttttccggg gatgtgtatg tgtgtgtgca gaggtggata ggtgtgtgtg    7680
cacagacacg aatgtgtgtg tgtgttgtgg gcagggcct  atattagtcc acagagaatt    7740
aaaacaaaac tgtccagtca cacaaaacag ctttctctgt actttaaact agattgacca    7800
gtgaccatga gctgagacca aggtctcagc ttgacatagc tttctttctc tagtgtgtta    7860
gacacaccac acacacacac acacacacac acacacacac acatacacac acaccctac    7920 ctgatattct ttagactcct gtctcagaaa gaaatgaaac cttccttgca ctcattacat   7980
ttcttaaact cttatgggtt acccaaacca aaagtaatta agggataaat gagatggaag    8040
aaacagttgg aaataaatgg gatatctgga gattggtaga tattagatta catccagcag    8100
agcctgaaag aatgaacatt gcaatttaat aagaagattc agaaaggttg tttagtatta    8160
atattgacag cttgaaagat agatttgctc aacaaaaggg aaaactgact caattatgat    8220
aacagatact gttcactaaa atcagaaata tggacataga ctggatgaaa cataagaaat    8280
atggctggga ttacagagtt aatggaaatg ccctcagacc ttagatgaca tttttttaaa    8340
taattcggtc gggattgccc catctttttt gttttgaccc caatcaaaaa ttggttctct    8400
tggaagagga ttttttcctt ttaaccttga aannnnnnnn nnnnnnnnnn nnnnnnnnnn    8460
nnnnnnnnnn nnnnnnnnnn nnnnnnnnnn nnnnnnnnnn nnnnnnnnnn nnnnnnnnnn    8520
nnnnnnnnnn nnnnnnnnnn nnnnnnnnnn nnnnnnnnnn nnnnnnnnnn nnnnnnnnnn    8580
nnnnnnnnnn nnnnnnnnnn nnnnnnnnnn ttcctcccctt ctttccttcc tccctttctc    8640
cctctcttct ttgtcttct  tcttccattg cttgctttt  gaacattgtc ttccaattac    8700
ttttcatcac cccttttaat tacttacaaa cccagaaatc tctgacctgg ctgttccact    8760
gccttctgat tttagctga  ataaatgatg attcctggtc atttctctcc cctaggtgt    8820 gtatgagtga gaaattctgc agcaccctga ggaagaaagt taacgatatt gaaacccaac    8880
taccagcctt gcttgaagcc aaaatgcatg ccatatcagg taactggcag tgtaggagac    8940
gttgaagcta tccaactaaa ataatgacag ctaccagcgc atcgtgtttt gtcctcgatg    9000
aacattccac tgttattatg tcattctcag acatctgaaa gcttttctgg gaagtttcac    9060
taatatgcac ataatatagc acaaggtgtt taagtgagta ccgtatttgg gacttctagt    9120
tcctgtttct tgaagagttt agagactaaa tgtactctgt gtgccatatg attctagcag    9180
atgtgtatgt agcattgtgt atctgtaaat actgaatgag gattattggg tgtgatcaga    9240
ccctttctat agagggaagg atggtgacat gagacaaatt aatgtcctca gtttgaaaat    9300
ctagtcatag aaacttggcg aatcctcaaa ggattatgct ccctcttact ctggcagtta    9360
ttaaggaatt gattttttcca ttaattagta gcttgaagtc aagagtctct gaaaacagta    9420
tcttatccta tcattagtgc tttcaaacac tcctctggat ttgttatttt attttcacaa    9480
ttgctatatt aggtagatgg gagagagacc gtgatccgaa tggactgatg gggaggttga    9540
ggctgcggga tgtgtccttt ggttaaggtc actcaattag ctaagcagtg gcagatctgg    9600
ggctaaagtc caggccctct ctcggtgtat tatatatgga ttttaaccc  agttatgtaa    9660 tgacagcttc aaaagttct  ctgagttta  taggttgaat ggaccagag  ctcatcagct    9720 tcaaagaat  cataaaaatt taacaaaag  ttataataat tacatgtatg tgttttaaat    9780
ggtattttaa gaaggaatac aataattggc agcttctgct cctcgagatc ttaaacaact    9840
aatgttggca gctaaagagc aatttggtcc ctggtgcagt cacgcgtatt atttacaacc    9900
agtgaaacat ggcagcgcaa atgtgggggct tggctcttaa cagcttcaca tgccatttac    9960
ttgaaattat gggcccattt gctgagagaa aaaaaagaa  gattgaacac agtcttgctt   10020
```

-continued

```
ctgagttagg gttttttgcct ttcttaatca atatatcttt cccaggaata ccggtggatg    10080
agtctgtatt aagcccaagg gaagaaatgt ataattcagg cagcagagat agcctcactc    10140
caatgtgaac aatctctctt cagactccag ggaaaatgcc caagatggta tattgcgtat    10200
ggcgcaggtt tcctgtttta gctctttggt cagctgagaa aattggtgag gcctgatctg    10260
ctgaaggatg acctgaatta accctcctgg taactgacct tttgacctca ctattttctg    10320
gttgctctgt atgctctttg gtggaccggc ctttcagtca atgggctgtc cccatgggtg    10380
atactagtgt taaggtggtc aacatttgtt tgcaactcct gcatataatg ctatttctgt    10440
ttcctcctgt ttcaatacct tcagaatggg caaaccctca ctccattagg taagattctt    10500
aaaagcccta ttgaatggaa aggatcttgg tttttttttt tttttgagtc agagtctcgt    10560
tcagtcgccc aggctagagt gcaatggcgc gatctcggct cactgcaagc tctgcctccc    10620
gggttcatac cattttcctg cctcagcctc ccaagtagct gggactacag gcacccgcca    10680
ccacgcccgg ctaatttttt gtattttttag tagagacggg gtttcactgt gttagccagg    10740
atggtctcaa tctcctgacc ttgtgatctg ccctgaatgg agaggatctt aagggaggtc    10800
cttaagattc ttagggggtc ttttgtctct cttcaagttt ctatgattcg cttagattta    10860
tagactgatt gatatggttt ggctctgtgt ccctacccaa atctcatctc aaattgtaat    10920
ccccacattc aagggaggga cctggtggga ggtgtttgga tcatgagggc ggtttccccc    10980
atgctgtttt cgtgatagtg agtgagttat catgagatct gatggtttaa caagtgtttg    11040
gtagttcttc ctgcattcat tcttcttgcc accttgtgaa gaaggtgcct tgctttcccc    11100
ttgccttccg ccatgattgt aagtttcttg aggccttcct agccatgggg aactgtgagt    11160
caactaaatc tgttttcttt aaaaattacc cagtctcagg tggtatcttt atagtagtgt    11220
gagaaaggac taatacatcc atcctgactt tgatctatgg cctgaggtcc tttcttaatt    11280
tgagaactat ttgccatttg cagagagtag gaataacaaa ttagtttcat tttcaaacct    11340
ggccagatct agctccttta catgtaacag tttattcttt aattcatctc tcttctcttg    11400
catttcatca caggcattga caggaggtca gtgggcactt ctgtattctg cctgaaaatc    11460
tccttggatg tctaactaca attattaggg actctttttt atattgcctc agttggtaac    11520
tgagtgactt ttttgccact acaaggatct ttttttttct agtttctgat atatttttct    11580 tactttttc tatccttcac ggaggcccat gaggcttctg cctactacca agtcccaaaa    11640
ccaatgcctc gattttagga ttttgttaca atagtatccc atatccagat accaaaatct    11700
attttcatta tctactgctg cctaataaaa aataagtcac tttaagacgt agtgacttaa    11760
aatattacca gttatttatt ttgcccatgg aaatacaatt tgggcagggc ttggcaggga    11820
cagctagggt ggctcaactg gggtgggaga atccacaccc aagacggtgc atacatatgg    11880
tctggctgtt gagtgctctc tatgtgggcc tctctatagg cagcttggct tccttacagc    11940
atggctgctg ggttccaaga gcaagtgtcc caagagaaag gaaatggaaa tttcttattc    12000
ttaaggtctg aattcagaca ctggtatgca tctctattaa tgtgtaataa gtggctcctc    12060
aaacttcata gcttgaaaca acaaaccttt atctctcaca gtctctgaga gacaggagtc    12120
cagagtgact tagctgggtg gctctgactc agggtctcat aaggtcgctg ttaagacaca    12180 cttttggagct gcagtcgtct aaaggcttgg ctggggctga aagatctgct tccaaactca    12240
tgcatgtgtt gttaacagac ggcttcagtt ccttgccaca agagctgtgc cctaggacct    12300
cttgcaacat agcagctgat ttcctcagag ccagtgatct gagggagaga gaccaaataa    12360
```

-continued

```
gacagaagcc acagatgcca ggcgcggtgg ctcacaccta taatcccagc actttgggag   12420
gccgaggtgg gtggatcacg aggtcaggag atcaagacca tcctggctaa catggtgaaa   12480
ccccgtctct actaaaaata caaaaaatta gctaggcgtc atggcgggcg cctgtagtcc   12540
catctactcg ggaggcggag gcaggagaat ggcatgaacc gggaggcgga gcttgcggtg   12600
agccgatatc gcgccactac actccagcct gggtgacaga gcaagactcc gtctcaaaaa   12660
aaaaaaaaaa aaaaaaaaa agccacagtg tcttgttagg acttagcctt caaagtcaca   12720
cagcatcact tctgcttagt gactagaagc aagtcactaa gttcagttca gcccacaggc   12780 aagggggaagg aaacaggttt taccccaaag gaggagtatt aaagaatttg gtgggcatat   12840 tttataacc actgcagtgt tacttccatt gtgttttatt ggtccagcat tcctggtgtg    12900
ctgattcaag ggaagggcca ctataacaag tctcaatgag aggtgtgtca aagagtttca    12960
gtgccatgct ctaaaagtg ccacagtatt tattgagaca aaggatttt gagaactgaa      13020 gacctggaca gagagctttt cagtcagagg aaatggcctg ttccatttat ttactgaaaa   13080
gaaaaatatc atggagcatc taggaagtgt cagatctggt tctaggtact gaggatgcag   13140
tagagaacag gacaagatcc cccttccttt tttttttttt ttgaggcaag gtgttgctct   13200
gttacccagg ctggagtgca gaggtaagat catagttgac tgcagccttg aattcctagg   13260
ctcaagccat ccttagcctt agcctctgga gtcacgggat tataggcatg agctcctggc   13320
tcaatgtctc ttcttttttg atagctgtgt tctcccattg ccacagtgg aatggagcta    13380 gatatgcctg ggctgaatat ggaggaaaag ctcagctatt tcttcaggag gaagagtagt   13440
ctagattggc ccaggtatag gattagtatt gtggtagctc ttcagagttg gttaggacca   13500
ggatacacag agctctgaat tgtaggctaa ggataagagc attttaggga gccattacca   13560
tgttttagcg gagtagtgac atgattaaaa ccagacttta ggaagcgtaa tccggccatg   13620
ttgtacacag agggatggat gtggcaacac cttgggagtc atggaattaa ctaggatgtt   13680
agaaatgaaa aaaggaagaa agtaggcta gtataggaaa tctactacag ataggtaatt     13740
attgattttt ggaagaacca tgatgatatt aatatatcca gttgagtgtg gtgtaataca   13800
cattaagaaa agtaatttag agagcccatt gtttctctcc cttttcactg tacacacctt   13860
aagtgtgttt tagtcacctc ttttttttcca ttctctattt ctgtttcaat tttcctgttc   13920
agcagaggat agtttggttt aaagccgata gcaaagtgg attctgttgt tgctgtcctt    13980
cctagacata tcagtccgtt ctcacactgc tgtaaagaaa tacctgaggc tgggtaattt   14040
ataaagaaag gaggtttaat tggcttatga ttctgcaaat tgtacaggaa gcatggcagc   14100
atctgcttgg cttctggaga ggcctcagga aacttacaat catggcggaa ggtgaagggg   14160
aaaccagcac ttcacacggc cagagcagga ggagggggt ggggggaggtg ccacgcactt   14220 ttaagtagcc ggaccttgtg ataactcact atggcaacag catcaccaag agggatggtg   14280
ctaaatcatt aatgagaaac tgcccctatg atccaatcac cttccactgg tgctaaatca   14340
ttaatgagaa actgcccta tgatccaatc accttccacc gggccccacc tccagcactg     14400
aggattacat tgcaacatga gacttggatg gggacacaga tccaaaccat atcactagtg   14460
aaggaaagta cagccctgag ctctatgcat actgacgtag aggaagaaac tcaccagggc   14520
agagagattt ctcagttttt gagtgcaggg gccatacagt tagtagagag aaacttgggc   14580
tttggaatct gagaagtgtg tgttcaagtg cagctttatc atgacttggc tggatgatct   14640
tgggcaagtt gtttaacctt ttcaggtctt gtttcttcat ctgtaaaatg gagctaataa    14700
taatattgcc catcacatta ggttgttgta agaattaagt gaggtagtaa attagaataa   14760
```

```
tgtggtacat cagtatatta atacatgaga taataaatat atgaacgtga cgtggctttc   14820
cacagagtga atacatgctt agctagtgat tgttagccat gcatctgagt tgggggagac   14880
ccagccagtg ggtgactctc tgatcaggtg tcactcagtg ctacaggttc ccggccagtg   14940
tacctgtagt aaaagggcag cggtggcatc catacctctt aatccaaggc agctttggcc   15000
tcagtgcctg tgcagtctcc tgactggcca actaggctgg gccacttgtc aatggggtgg   15060
attcgttttt ttgtttggtt ttcagctccg agttcaaaag cctgggagac ctgctggctt   15120
ctctcccaga cctgggcccc atattgttaa cctgggccct ggaggtctga tcagtgtcct   15180
ggctggatcc agtgcagtaa gagaagccaa ggagaagaca gtcttccaag gcctgaagca   15240
ggtctgacct aactgcccaa tgtaggaggt ttgccctggg acaaactaag gtcctgcagg   15300
gttcgagggt gaaaggcctc ttctcccagg aggcagcccc agacccacct tgctgaactg   15360
gctgcctgga aaggaagtga gagcgaagat ctcaaaaaag agcagctctt taacctctgt   15420
gctgctctca ctgaacgctc ccgccctctg cccaggactt gatggctttg ccctggccc    15480 tggggcagag cgaagggaaa gcgtcagtgc cctctagggc cgagagtgtg gcactacagc   15540
aagtgtgtgg tgggtgcggc tgacttgtgc tctgtggcta ctacccatcc ccatcagaaa   15600
cctgggcctg tttccttctc tggaatggtg ctgggacttt ccaaaccacg gacctgtagt   15660
gatgagagtt ggtgtcttga gtccgcgtcc accgtctgca tgccatgcct gccttcccac   15720
tgctgggggc cctcaacccc tctccagttc ccgtgtctaa gacttagcaa caagcatcct   15780
tcctgtgtgt tggactgcgg gtctgcacca ttgtgagaca cggtcctata ttgggcccta   15840
cctctatcgg tgctcgttga cctgactggt atcacagtcc tcatctggaa cggggccagc   15900
caagctctgg ccactccctt gtcctgggac gaaggctcag cccctgaggc ccggcgagta   15960
gtcaaggctg gctctctgat gcctggctgc tctgatgctg gcatcctgca tgcacttcca   16020
gctccagcct tgtcctgctc aaattacccc tcattattga tctggtccat ctgttgagtc   16080
accctccagt ttttttcttc cactttgttt aatgcctggc actcaaaaga cagccagtag   16140
aagtatttgt ttttcaaaaa atggaccctc attcattggt tgctgatccc tagaatctgt   16200
tgttttcata cctccttcac ttgttaagat tttcatctcc tgccctgact tcagtgggta   16260
cgtctggttt taagccccgg tcctccttct cataggatcc atcctctgtc aggtgattgg   16320
agctggctga tgttccagct tctggatgct ggaagccagc agcagcagct gcctgggtga   16380
cagcctcact gtgtgttggc aggcttctca ctcacctttt ttaatcaatt ggacctgaaa   16440
atcttgaagc taaacaaaca cagccctgct attttggcac aagatgaagg ccagttttaa   16500
gtggtctata aaagctgtga aaaaaacttt taaaagagaa ttatatccag ggcacccaag   16560
ctgcttccag atgccagagg cagccctgca tttaataata tgcttgctgg aatccctta    16620 aaatggtaga tgttggccat ctttttcttt tttctttgca ttcccaatgg aaggacttcc   16680
aatgtatggc cctggtatta ttccctgtat gttttagaga agctctaaat tcctgtagcc   16740
gtcaaacttg ggttttttcac tcagactgca tgttaggatc atctgggaa attttaaaat    16800 actggtaccc aggcagcacc aaattccttc ggtcagaatc tctagggatt tttcctgaat   16860
ataggaacct tcataaacag tttccaggtg gtttaatgt cctgtgaggg ctggaaccac     16920
cgtaccagtg agaggagagc tggcctgccc tgctcactgc tggcagatgg actcttgagt   16980
cacatctttg cacacccaga agctccaggc ccaccgtgta ccatggctaa gtagctgcaa   17040
ctgcaacctg gccttggcct ggaagcacat cttgtaggat cactgatgtt actctcccct   17100
```

-continued

```
ggccttcccc ttgtcctgga agatgtgcct aaggctgaga gacttcattg tttaattcat   17160
ctagctgtct gttctgagag cccccagcta aactgaggtt ccagtcccag aacagctagc   17220
aaaccgccct aagggaaat gaaggggaga tggacatggt atttactgcg tgcctttcat    17280
aggatgctgc ttttacctgg tagatggccc aatgcctagt tgtctgacct gtgaccaggg   17340
gctcctcgcc tgggaaactt gtttatatgt ctttgtggct cttgcctttc ctgtgttcag   17400
tttatgcccc cctgcccatt gctctggcgc tgggagccaa accttgtgct ctcttgggca   17460
tcccaaggta aaacctggcc tgggcattc cctggtcttc agatggaagg tgcaaaggca    17520
atatacacca cagtaggaaa caaattcaaa agtgtaatt tacggatcct gggcaggag     17580 ggcacagaga gtcgggaggg cagtcctttg tccctgggcc actccagata ggaatgaagc   17640
atcatgcaga gagagagaaa caaggcacat ggcaactggc agtgtgtata gggagtaggg   17700
tctgggccac tgtaagtttt caggcaaatg tgtgaatggc ctgtttaaag aagcaatgg    17760 ggaagcaggg agcccagtct gctagtcagg ggagatgtct ctaagttttt atctctcgcc   17820
actggcttga gccattgggt gtggtttcct tctaatgcct gggcagctgt gtcattcccg   17880
ttacagtcac cacatgattc taattgcctt agaatttata ggaaccagtt ggcagcccaa   17940
caagtgggct cctctggcca gtgagggagc ctggtgaggg aatcttccca ggacaggcag   18000
agacatctgc ctggttctta gattggccat ctttggtctc acctcagttt ggatatattt   18060
ttttttttat ctcacctgcc cccttggtat ctggttccaa gaagcaaaca gctcaaataa   18120
ttatttattt taaaataaca taagaggatg tctctgatac tccaaaaccc tttttttttt   18180
gaaaaaaaaa aaaaggatg ggttctatcc aatttggcat ttcatttata gagaatagaa    18240
actatctata cccaaaaatg tattcattgc acacaattgt atttgaatgg cagctggaaa   18300
tcttctctcc taactgatgc ttttggggaa aataagaaca tttggacaat aaactagatt   18360
ttctagataa acacaaaatg ggtgaatttc acacatccaa taatgaaagt agttttttcc   18420
ttaaattaga aacaaggatt taaatttccg tcttcttctg aatgaatatt tggcacccaa   18480
ccaagaaata tatatcattt taaattttct tgaggaaata tccttttctt gcataattaa   18540
tttaaaggaa attaaattga ccatgtcaat tgtcaaacaa ggaaaagtaa gaattttgct   18600
tatttgttat taattttatt tacaatagta tttaaaggta actttgtaaa ataaccccta   18660
atgatataat ctaaaataaa atagattgta tttaaatcac tttttttatta tataccacga   18720 aaaactactg aatgattaaa acattcttaa gtgggttctt aacattgtat ggaactggaa   18780
agagcagttc agatcacaga ggcatgggca ctgtgttcta agtggtcact gcactgattc   18840
agaacagcag gggctggctc tgtactgggt gggtgggtgc tcaaggccag acctacacag   18900
tgctcctgtg tctgcagctg cagggaagca ggagaaacag tgacgatggt ccaggagagg   18960
ccacctgaca tatggcagaa aaacaaaatt cagggtacag acagtggctg ggagcatcaa   19020
ctcaatcgct ttcttctttt actattttcc ctctttctaa aaaagtctgt gatttagatc   19080
agtggctgca ggagggagac aagagaccca gtaaagatgt tttcaaagat gatgcctatc   19140
tggtgtgaaa agaaatgaag acctacccaa agagaataag cacaagctat tatgcagagc   19200
ttgctacagc aagggagtca gacaccatca tttgcaattt ggcagagact caaaggtggg   19260
cagacgagtg ggagagcttt atagtggaaa aaggcgaagg cttcaggtgt gccctgattg   19320
gaggttatca atgcggggaa gctggaggcg gctcactaga agcgaacatc ctgtgtgctt   19380
ggtcagggga ccatatttgg cttttctctg ggggtcctaa gttggaatcg gggacaaaaa   19440
ttagggaagc catcagttat taatccagtc ctgaacattt tgagtcaatt gttacagaag   19500
```

```
ttattattta gcttcctgga tagttactag agagcaattt ggcttccagc aggtctgatt    19560
tagagcaggc cagcttccgg ggttgctttt tgtgggtaag ggtattgttt tctgggaaag    19620
ttgctgcacc ttgtggatca gagttccatc ttttgctatg gcctggctgt tgtccgattg    19680
tatatttagt cagtcaccag gcaccacatt ttctcaagct gttggaaagt tctgtgggtc    19740
cagtgttatc ttcccttgt attctatgaa atatatggct gtctgaaatg tttgatgtgc    19800
aaagccagcc atgggctct gctcacagca aatgcttttg gctatctcag gaagtcatgg    19860
tgactggaag aaatgcacaa ccctgacaga aaatggcaaa ttctagctga agggacctcc    19920
agggagaagg gggttgggga ggggagcagt tggctggggc ttcttggccg cctccattgc    19980
cctttggttc agccagccca ggctcacagc agatatcctt gacctcgcca agggaaggct    20040
ctgaaagaca aaggtagatc ttgatcttgc ttaactgtgc acttgagctt gcagttcctt    20100
gaaagatctg tgtcacgca agacaaatta tacagcagtc tactatttct ggagtttgat    20160
cattctcagc actggcttta tttctttttt tccactaaag aagtatagtt caaatgtgga    20220
taggtgaaag tagataatct taggaggatc gttacaaact gaaatgtcca tgagttcagg    20280
aaagtgccat gtgtgtgagg ggtaccccag gtgagaggcc tgaggattgg gcaggtgaaa    20340
gggaccatgt gggcacagga ttcatccccc tcaccatgtg ctttctcact ttagtgatga    20400
tttctaccca ggtgttgact aagtcactta ttgacatgag atcagaagaa acaagttcaa    20460
gttcaacaat ctccgcatgg gatcttagaa ctctgaaact ctgtgacctt cacaaggtta    20520
cctctgggtc tagattttt aactggaaat caaggacaat cattaagaga ctcccctccc    20580
tggattgttg ggaagattaa atgatacaat ccaagtaatg agagcattgt agtctctaaa    20640
attggattct caaataatga cctcaggtga aggaagaact gttcaaaatg ccccaggtgc    20700
tatgaagtac agagggcagg tattttttt aagggatggg gtcttgctct gttgctcagg    20760
ctacagtgca gtggtatgat catgactcac tgccacctca agctcctcgg ctcaagtgat    20820
cttctcacct cagcctccca agtagctagg actaaaggtg cataccacca tgcctggcta    20880
attttttaat ttttttgtag agatggggt cttgctatgt tgcccaggct ggtctccaac    20940
tcctcaagca accttcccat cttggcttgc caaagtgctg ggcttacagg tatgagccac    21000
cacacctggc tgatatttga attcagagat gctgaggata agtaatgttg gaacagagtg    21060
ggtaaagtca gcttcagcat aaattgtgtt tatttaattt aaacacaatt taaattttgt    21120
gttttggcta tctcaggaag tcatggtgac tggaagaaat gcacaaccct gacagaaaat    21180
ggcaaattct agctgaattt taaattgtgt tatttgcgga ataaaatatg tggacaagtg    21240
ctttaaaaaa cctatgagaa tacccaggtt tcattccctt gttgagagc aggcgggcac    21300 aggcatattg ggatgccata ggtggcatat tcttctccac acacatcctc cttggcattt    21360
agaaagggcc tgtgaaagtt atgaagattc aggtcacaga tctctgatgg gactttcttc    21420
aggtatcagc attgactttc caaattttca tcactgagct cctgaccaat ttcagcagtc    21480
agagaggtct gcatcaagca aggtcttggt ctaagcctca tgggattaga tctgaggtca    21540
aaatgcctcn taaagtatta atcaagggca ttgtagcatt ttctcatggc ttgggtcttg    21600
atatgaatgg tctctttggg aattcacact cactctgctc ttttaaaatg ttcacttta    21660 tcactgtgca ttttcccaag ccttatccct caggatcaaa gaaagggcct aggctttaat    21720
taatgatctc tcctgtgttt taccaagggc actggtctct cgagcttgca gtgggttgca    21780
agggattaga gggtgtattt gcagcaaaac ttctgtaccg gcactcgctc tgtatatata    21840
```

-continued

```
gtctcttcca atttgctttt agagatctttt tctttctgac tgtttgcagg aggacatggc      21900
acgctgtggc atattctgcc tgatgtctct ggaggcatag ttggtgccca tcccactttt      21960
tattaactct cttggttgaa aacacagccc agaagacatg ttgggacttc ataagcacag      22020
cctaaggagg aacattggaa ggtacaacat tgtacatgtg gccaccctgc cccaacgcag      22080
tcacacctct gtgctggtcc tcctgcgagc tccccagagc atgggtccc ttgaggttct        22140
ttgtggcatg cggtaggggg ctcgatcctc agcttccttg acttggccat tgttcaggat      22200
ggaaattacc gatccgggaa aagttttatt tgaggttact gtttacagct tgaagctcat      22260
ggaagtgcag tctgctctcc tgtggactttt gtgggttttt cctaaatggg tccaacccat      22320
cagcttggca tttggggcac tattgttttg aagcaacttc cttgtgagtt tagtctcacc      22380
tcctacccct tgcccattgc tctctaacct gggttcctgt ttcttctttt gggactctta      22440
tattcttccc tcctgaaatc tgcctcagtc tctccttctg gaataatctc tcttctcctc      22500
tgacctctcc tagtatttgg ttttttctttg gaaggcacct tatccccttt attttatggt      22560
aacttcctgg agagcaggag cagtacttgt tctcttttgt gcttgtcatg ttgcttaaaa      22620
cacatgagtg ttttaagcag tgagagacaa acacatgagt ctcaataggg tctttatcca      22680
atcatggcat tggaaactat ggacttcagt gacagatgtt atgtgctagg tttcagaatg      22740
cctttaaggt gggaaaacat tttgtatcat tttcaacatt tgtatcagtt tgaaatctgc      22800
ctgctaagta acaataaaaa agttagcaac ataatttatg tttaaaagga agtgttctgg      22860
ggtgatgttc gagttggaaa cttgccctat gctttactgc attgtgatct tcagcaagat      22920
attttagttc tccagatttc cgctttccca gctgtaaaag gagacaacaa tatgaatttc      22980
agtgaacata aaaagcaccc attatttttat acattgcaaa gaagaaaaaa ttgctgtcaa      23040
ttaagcagta acagtgcttt ctatggttta gaattttat cttatactta actgatatag       23100
ctcttttaga tgtatttagg cttttgaaaa atcacatatc actcattaaa aaggaaaata     23160
aattggttaa ggttttcctt ggcatcttct tcttcattct gagtcttccg aaacacattt      23220
ggactcaatg ttgtcgaggt ttgtgtttcc ccacacgtca tcatcctgtg aaccattgaa      23280
gttgatggga ggcaacttttt tctcccccaa gaataaagag ttttctgtag gattgtctgc     23340
caaactgcta acacctttct tcaagttttg aatgctggtg cttttcccagt cttacaaatc      23400
cacatcaaca caagattttc aggcaacagc cagtacgcag atggtcctaa aatagtttgt      23460
acattgaaac accagggggt tgcagatggt cagccaggcc agggaaaata atccagttat      23520
aaccactgca tcctgaccac ttcctggctg atggtgattg taggacacat ccctgtttca      23580
gagatgttaa aatgtaaaat aataataata ataataataa taataataat aataatataa      23640
gatataacct gtttcctaaa gttgtgatga catttaaagg tgagaaagtt tgtagctatt      23700
attgtgatta tggttactat aaattctgag aaaacacagt ggggttttct aattaacact      23760
aactaattta tgggacactc attaatgtta tatatttatt tattgttcaa tgttcatgct      23820
taaaaatttc ttaattttttc ctcttttttaa ttgaggtatg gtttatattc agtggaatgc      23880
acaggtctta agtgtttaca gttcttgaat tttgacacct tgttacgaa cagccctacc        23940
aagagataga acagtctcat cactcaagaa acaacaccct atcttgtccc agtcatcatc      24000
gtccctcctc tgttctgata tcttctacca tggattaatt ttggctgttc tagaacttaa      24060
tggaatcatg tggcactact ctttttgcatc tttttctaaag acatgtacat gttggctggg       24120
cgcggtggct cacgcctgta atcccagcac tttggaaggc tgaggtgggt ggatcacrag      24180
gtcaggagtt tgagaacagt ctggccaaca tggtgaaacc ccggctctac taaaaaatac      24240
```

```
aaaaattaac tgggcgtggt ggtgggcact tgtaatccta gctacttggg aggctgaggc   24300
aggagaatag tttcaaactg gaaggtggag gttgcagtga gctgagatcg taccactgca   24360
ctccagcctg ggcaacaaga acaaaactct gtctcaaaaa aaaaaaaaaa gaaagaaaga   24420
aaaagacaca tacatgttgc tgcatgtatg acgagtttgt ttcttttat tgctgagtag    24480 tctttcattg catagctata gtattatttt tgcatcttcc tgctgatgga tatttaggtt   24540
gcttccagta tggggctggc tctcaggcat aagacactgt gaccatttat ttgagtgcaa   24600 atattttga tgacatgttt tcatttcttt tgtgtaaatg cctggaagta gaattgttgg    24660
attaaagggt aggtatacat tgaactttat gagaaactgg cagaactttt cttgaaggga   24720
ccattttaca tgcgtgagag ttccagttgc tccatacctt tgtgaatgtt gacatttta    24780 gttgagttaa tttgaaacat ttgagtgggc ttgtagtgga atatttatgg ttttaattt    24840 tcttttctta atgattaatg atgtcaaatg ttttttcata tgcttattag ccatttgtgc   24900
gtctactttg taaatgcct gttaagtcat ttgaccattt ttcaatggca ccatttgtgt    24960
tttaattgtc aagttgtagt attcaattcc ttgtcagtta aacataatgc aatgattttc   25020
tccaagtctg tgacttgtcg tctcattttt tagttgtgtc ttttgatgag aagtttttaa   25080
ttttgataaa gcccatttat ccttttaaa atagtgtttt ctgtatctta tctgaagttc    25140
ttgcctactc caaagtcaat caaatattca tttttttttt gtagaagctt tatagtttta   25200
acttttacat gtaggcctgt gatccacctt taattaaatt tttgtgtggt ttgaggtatg   25260
aatcaaggtt aatattttt ccatgtagat agctagttgt tccagcacca tttattgaaa    25320
atactttctt ttcctcattg acttgctttg gcactttggt tggctgtata tgtgttaatc   25380
cactcctgga ctgtttattc tattccatcg atctgtttgt ctatgtatat tcaatgccat   25440
attaccttga tttatagtgg ctttagcatt agtcttgaaa ccaagactca cttttttaagg  25500 attgktttgg gtcatcctcc tcctcctctt ccttcttctt ctttcttcct attcttcttc   25560
attcttcttc gtcttctcct tccttccctc cctccctctt tcacctcctc ctcctccttc   25620
ttcttctttc tccctctcct tctttgaggt ggggacttgc tatgttgccc agacaagagt   25680
gtagtgcctg ttcaaaagtg caatcatagt gcactacagc ctcaaactca tgggctcatt   25740
cttctagatt ttatttgttt agatatgaag tctcactctg ttgctcaagc tggagtgcag   25800
tggcaggatc tcagctcgct gcaacctaca cctcctgggt ttaagtgatt ctcctgcctc   25860
agcctcttga gtagctggga ttacaggtgc ttaccactgt gccagattaa tttttatatt   25920
tttagtaaag atagggtttc gccatgttgg ccaggctggt cttgaacacc tgacctcaag   25980
ggacccacca cctcggcctc ccaaaatgct gggattacag gtgtgagcca cccatgccca   26040
gctcactttt agacgtttta gaataagcac ataaatttct acaaagaac  ctcataacat   26100 tttgattgga attatattaa atcaatgaat caatgtgggg aaaattgaaa tcttaccaat   26160
attgaacttc cagtgtatgt atacagtgta tcttttaaat tatttgtctt taatttgttt   26220
cagcagtttt ggaaaaatag ttttcactgt agagctctgg cacatattta agaaagtat    26280 ccctcagtat tatgagattt aaaatatttt gtaaattgta ttttttaaaa aatcatcttc   26340
tagttttttg ttatttagac ataagattga tgtttgtaca ttgaccttgt atcctgcaat   26400
cttgctacat ttaatttatc atatattttt ctcagtgctt tacagaattt cttgtttatt   26460
cttgtaacta cctatgagtc aggtgttatt gcaattatat tttataagaa atttgcccca   26520
gatgtgctaa ttttcttgct ccaggtcaca caatttgagt aacaggggag gaatttaatt   26580
```

```
taggtcaact ctgattatat ggcccagtcc ccttccacac tgctataata tgtcatctct    26640
ttgacatttg tatattattg gaatggagtg acacattgtg gtttctctgg attccactgg    26700 gacattttg ggtcatcata ctttacggga gatggcttca ccaatggaac tcctaaaatg    26760
gacataacaa gaataaggtg ataaaaaaga cggtgatttt tccagtttaa ggggagcaat    26820 attttttccag gttctttccc cagaggactg ctaaggaaat tgwacataat ctcaaagtgc    26880
agtttctttg cccatgctgt gaatgtacat tagctgctgc tagatcttcc atgtgtgtgg    26940
atgctgtaaa gcttgttttc ccttcttctc tcccacaacg tgctgtagga aaccatttct    27000
ggacggctaa agacctcacc gaggagatta gatcattaac atcagagaga aagggctgg    27060 agggactcct cagcaagctg ttggtgttga gttccaggaa tgtcaaaaag ctgggaagtg    27120
ttaaagaaga ttacaacaga ctgagaagag aagtggagca ccaggagact gcctatggta    27180
ggtagtgcac aactgttacc ccggcaagat attgatgata tttgttgtgt tttgtggcca    27240
ggcagaatgt tctgtgcctt watgtgaacg ttcactgtga agagcgtcat ggagcacatg    27300
gcccttttcc cttggggaca ttttttggcag gtgccttggc aaactgaatg gaatwacttg    27360
tcagcttttg ttttcatatt cacatgwgac atcttttctt tttctgttcc ctgtctcaac    27420
ctgtgtttgc taatagcctt gttattattt agagcagtct ctcccttggc aaggtcttga    27480
gcattttctt tgtgtgacaa ttatcttcct tttgtcccctt ggctccgtct ccttgtstgc    27540
acaatcatag actaaatcag gctgatctga gaaaattgag ggaagaccat aaagtggctc    27600
ttctatgtgt ggacttttct gagagcttct tccccagga aggatgatgt agaagatgtg    27660
aatgccgcct tagccaaagt gtctgcttgt cagaggagtt caagtgttcc tgtgttcttt    27720
ccttttccag tcgttaggag taactgagct tactctgaga tttgcaccca gagggatggt    27780
ctcagaagac gctggttcag tgcaaattga gatggtaaaa acttatttct taaaaaatgg    27840
ttcctaaata aatgtcattt actaaaacaa atgaaagaaa tatatatatg aataaatggc    27900
tatattttac aaagtatgct tatttaagaa gaaataagaa aaaacggggc tgataggaac    27960
cagatttgaa ataggcttt tgtaaatact ccgtaaattg aagtaaatga agagtagtat    28020
ttataagcta gattgagaaa tataaaatca gctagctgaa gttaagtgca tcaatttggg    28080
atgaataaat tttcttttaa aatgtctatc aatttgtgta gagagaggtt tcttcataga    28140
gatattagaa tcaaagagta tgttcagtag ttattctgtc ttctttgtaa tgaataccct    28200
taagttggct taacagctca gtacttatct tttttctttt tcattcttaa aggtcaagcc    28260 ttgttttttgc catatatgta actagagaca gtacgtttga ggctaaataa ctgtagtact    28320
agggaatgac aacacgctca cccaagacac cgcagcctgg tttactctgt catgatagga    28380
atgaggattg tacatttgaa ataggtttct gctattgatt ttttaaatgt ataaacgatg    28440
gaaactacgg aatttctcat gttttcacca catgttttt tgtcataaaa tgaagaatat    28500
attatatcca agaatgaaga ggaagtgaac aaatttgagc aaatttagtc cagcaatatt    28560
ttcatttgaa tagttgagtc cctgaaagcc attaatatcc tttttaaaaa agaaccatg    28620 cagtattttt gaatctcatc attgtcactt cactaagtat tttcacaatg atgaataaaa    28680
cataaacaaa tggaatgaga gattgttacc atggatgatt ctaaattgca gatggctcat    28740
tactgttgtg aagcctctct ttatgttttt acacttggat tttgctggat cagccaccct    28800
ttccctatac attgatttac acgtgcttaa tttttttttaa ccaatttgag gtgagttggc    28860
tttaggtgaa ccaaattaat aatctagggt tgagagtgtg ggaaacaaat aaataatgaa    28920
ttcctgaata cattgaagct tttatttatt aaaatgtgat aaaactgggg caaagtccat    28980
```

```
attcagcttt ttttgtgttt tgagggttaa aaattcagag ggagctctgt gttcaagttt    29040
aaatgtagag aaagtacaaa ggagagtgta cttatgcaca tacacatatg catgcatgta    29100
ccatgactct tttagccttt agagaatgaa accatttaag aaatgagcaa tatgtagtat    29160
tcttaaaaaa agattttgat ttccaacaat agttgtggaa tgcagcgttc aggggaaaaa    29220
ggcaactcat ggatgatcaa gccaccctgc ttgtcaggaa cccagactct tctatcttgt    29280
tcttctctgc cccacaacat gtgccattca gtccaacctg gctgacccag ccacatgcat    29340
gtccaagtcc agtcagaaaa aaaacaaaga aggaagagag ctcatctatc ccctttaagt    29400
acgcttttag aaatctgcac acatctctgc tacggccaca tccctgtgac cttaaccttg    29460
ttatatggta acagctactt gcaagagggg ctgggagctg tccttaccct gggcagcaat    29520
gtgccccact aaagtgatga attctgtttc catagcaaaa ggggagattt gcagtcttag    29580
ggaacaatta gcagtgtctc tcgtacagag acctttaat gatgtgaagt gtatctctaa    29640
tgatgcacct gagatgaatt tgctgcatgc atcacttaaa atatcattgt atcttgtgtc    29700
tctggctaga ttgtgagtcc accgaggtca gaacattgtt cttaggtttc actgtactgc    29760
tttggtgtcc agcatgatgt ctttaaaat agtaaatata ctataccatc aatatttgtt    29820
catttactgg ggccagatgt taaaatgaca catgaatgag tcctctcttc ctgcatttta    29880
gattgcagat ctggaccttg aatcttctgc ttctttattc attttccaaa ttaatgaggg    29940
tagtgataag tttgtctttc ttggaaggtg cttgagttgt ctgagttgga tattcagttt    30000
ggagtgtcag taatagaaca atacggtgat agaaaaggaa ctgaaatatg ccaaggtact    30060
caagggcaaa gggagacaga cctcatcacc gaatccattg gcttttgttg ccaagacaca    30120
atctctataa agagatgata aacaagtgtg ctttaactcc tgtcagctgt tcttgagact    30180
tcaggataac acatttgaat tcggagcaat gttaagtgca gtgaaataga atgaaaagct    30240
aaatctatct tccaagcctt gaatatttat ggaaattaac tataaacatt taattattgt    30300
ggattccaat gtgtgtgttt atttaaagaa gggcggaatg aaaaaaatca gcaactttta    30360
caagtttgct acatctgctt ttacattctc tttttgagac aaaagttttg cttcttgcaa    30420
ccagcctgaa gtgtaatggc gcgaactctg ctcactgcaa cctccgtctc ccaggttcaa    30480
gcgattctcc tgcctcagcc tcccaggtag ctgggattat aggccagcta attttttatat    30540 ttttttagta gtgacggggt ttcaccatgt tggccaggct ggtctcaaac tcctgacctc    30600
aggtgatcca cctgcttagg cctcccaaag tgctggaatt acaagcgtga gccaccgcgc    30660
ccggcctaca actgcttttc aagttaaaag gacagccctc agatttacgc agcagttttt    30720
caccatccct tgtgtataaa ttggtaatct gtattgtact ttattaatat tgttgatttc    30780
gcactgtaac tcagctataa aggaaaccga cgtcaagggg agagatttaa tcacagaata    30840
atcaggacta gaattttaaa taggacatca ttagcatgtt aatgaatttt cccaccttat    30900
gccagctgcc tgagtagaaa agatactgca gatgtagctc aaaaatctgg ctggttccat    30960
ggcccagtga gctgtcagga atctgtgtag ggtgatccat aagctaagtg aagggattct    31020
aagtgagaat accaagcagc aagatttttgt ttttctgaga acgatggcta actgtgccca    31080
gcctaaactc atttgtcttt cggtgagtaa gaggggaatg ggaggcagag aagggcagt    31140 tgaagggcaa tgaggttgga gtagaggcac ctttccaatt atggtttggg attaggacct    31200
tttgctttag atagaaaagt tgtaagttct caatgacaag atcctgccct aattcttggc    31260
acagtctcac aattttgag cttgaaatag ctaatgaaag gaagcatgag tgtcttagtc    31320
```

```
catctgcgtt gctatagagg aatacctgag gctgggtcat ttataaagaa aagggaattc    31380
tttggctcac agttttgcag gctgtctaag aagcatagtg ccaacatctg cttctggtga    31440
gggcctcagg ctgcttccac tcatggcaga agatgaaggg gagctggcct aggcagatca    31500
ctggtgagag aggaagcaaa aagagagaga agggacatga cacactcttt ttaacaacca    31560
gctctcccag aaactattag agtgagaact cactcattga tgaccaagct attcttgagg    31620
gatctgcccc cagacccaga cacctcccat taggctctac cttcaacatt gggggtcaaa    31680
tttcaacata aggtttggag gtcaaagaaa agaaactata gcagtgacag attatactga    31740
gatatcggtt taactctgaa gttcccagat gcagctactt gcagaatttc acttcacacc    31800
tattaagaaa agtcttttag tttagaaatc ctgtgagtta caagttctgc atatataggc    31860
agtaattctt ttttccatat atgtcagata tatgtagaag aaacattgat gaaaaagtag    31920
aacaaaagaa taaaatctat gggtctcttt tattggcagg gagagggagg aaatggagag    31980
ccgggacaat acatacaaca aagataaaaa caataaaatt agcaaacaac aataaaattt    32040
aaaaacaaag acagaagaaa atgccaatgt caagtgttaa ttatttggtt gagaatatga    32100
tgtgataatg aacttcctag aagtcacagc aaagaagaca gttgaagcat catccttctt    32160
cctcaaaagc accttgaaaa gcacagagct ttttgggaat tcagagtgat gctaaattct    32220
tcaagacact tctcttgaaa gcatagtgga aagtcctcct gaacagattt ataacacatg    32280
cagaaagctc ttttacttgt attattattt tttacaactt tttattttag gttcaggaat    32340
acatgtgcag gttctttata taggtaaatt gcatgtcatc ggggtttggt gtccagaata    32400
ttttatcacc caggtgataa gcatgttatc cgatggttgt gaccaactac ctctaggaaa    32460
aaaacatgtt ggggatccct tcaaagcagg agggactgtg cacaggagag actgaaacca    32520
catacacatt ttagatatgt aggtatggac agttttccc acaaaaagat ccagtttttc    32580
agcagatttt taaaggggtc attctaagag tcctcaaatt ttaagaaaca ttaagatatt    32640
aaactgtcga ggtgaattag ggcttgggct agtgaagttt aaatacggca tcttccaatt    32700
tctgacatta tttcaagatg taacttagca cctaaaaagt ggctggagaa catatcctgt    32760
acactcacca aatgtcactt ctttcctctg agctttggct acgacctatg tataagaaaa    32820
cttagctctc cgggccagaa cggtgatagt gctcttgata acagagggcc aagccgtctg    32880
cttttggaacc agatgagtgt tgcggtgcta tgtggcaaga aatgtagatg tttatatggg    32940
aaatagatat gtgtctgcct ttccaaattc gaaatctttg gtcatttaga tttaaaaaaa    33000
tatgtcaaat aggatctttt ggaagaaata aaaaaaattc aaaatctttt ccctcaggtt    33060
tttctgatag gctgaagttt taaatctcta atcatttatc tttgatttgc cttattgatt    33120
acattatcac tttatcagga ccctgactaa atctgtttgt gtttttaatt tctctccatt    33180
tttttccttc cagttacatc cttgcatcac tattagtgtg attatttccc ttcagccatt    33240
tttgcctgtg aatttctaag cttgaaattt gcaactaact ttctccctcc tttattaagt    33300
cgctgtgata attcttttgg gaggcatcgc catacagtgg aaaaagcctg gattaggatg    33360
taggggtgt cagtttaatc tcagtcctgc ccttccctaa tcatctgcat agcacctgat    33420
atatatagca tcagaatgtg aggctcaatg agtgaatagt cttcagcaac tcactgaatt    33480
ttatctgagt ctcagttgct tcatatgtaa tactgtagaa ccagatcttg aagttgcatt    33540
tctatccatc catccagcca tccatccatc catccatcca cccacccatc catcctttcc    33600
acaagcattt attgagtact tacgatatgc taggcgctgt ggcaggccct catggtccag    33660
agatgaatta gatagtccct gtggctactg aggtcccttt taactctagc cccttgtatg    33720
```
tgaatttcca caattcaatt tatactttgt tcatttattt tcttgctctc agctactttt    33780

<210> SEQ ID NO 5
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Desrciption of Artificial Sequence: synthetic
      oligonucleotide

<400> SEQUENCE: 5
ggctggatat tgcccttgag ccataatt                                        28

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<223> OTHER INFORMATION: Description of Artificial Sequence:  Synthetic
      oligonucleotide

<400> SEQUENCE: 6
agaacagagg agggacgatg atgac                                           25

<210> SEQ ID NO 7
<211> LENGTH: 20
<212> TYPE: DNA
<213> ORGANISM: Human

<400> SEQUENCE: 7
caccgcgcag gtaggggagc                                                 20

<210> SEQ ID NO 8
<211> LENGTH: 20
<212> TYPE: DNA
<213> ORGANISM: Human

<400> SEQUENCE: 8
ttcttcccag gcagccggga                                                 20

<210> SEQ ID NO 9
<211> LENGTH: 20
<212> TYPE: DNA
<213> ORGANISM: Human

<400> SEQUENCE: 9
gcagatggag gtcagtgtct                                                 20

<210> SEQ ID NO 10
<211> LENGTH: 20
<212> TYPE: DNA
<213> ORGANISM: Human

<400> SEQUENCE: 10
accaacatag gtaatatcct                                                 20

<210> SEQ ID NO 11
<211> LENGTH: 20
<212> TYPE: DNA

<213> ORGANISM: Human

<400> SEQUENCE: 11
tatgataaag gtgagtttta                                                  20

<210> SEQ ID NO 12
<211> LENGTH: 20
<212> TYPE: DNA
<213> ORGANISM: Human

<400> SEQUENCE: 12
gggtttccag ctgagacgtt                                                  20

<210> SEQ ID NO 13
<211> LENGTH: 20
<212> TYPE: DNA
<213> ORGANISM: Human

<400> SEQUENCE: 13
ccactcagca gtgaatacct                                                  20

<210> SEQ ID NO 14
<211> LENGTH: 20
<212> TYPE: DNA
<213> ORGANISM: Human

<400> SEQUENCE: 14
ttgttttaag ggccagcgga                                                  20

<210> SEQ ID NO 15
<211> LENGTH: 20
<212> TYPE: DNA
<213> ORGANISM: Human

<400> SEQUENCE: 15
gcagctacag gtgagcaggt                                                  20

<210> SEQ ID NO 16
<211> LENGTH: 20
<212> TYPE: DNA
<213> ORGANISM: Human

<400> SEQUENCE: 16
tctgtctcag ctgcaagtgt                                                  20

<210> SEQ ID NO 17
<211> LENGTH: 20
<212> TYPE: DNA
<213> ORGANISM: Human

<400> SEQUENCE: 17
ccataaggag gtactgctga                                                  20

<210> SEQ ID NO 18
<211> LENGTH: 20
<212> TYPE: DNA
<213> ORGANISM: Human

<400> SEQUENCE: 18
attcttccag cctccaggaa                                                  20

<210> SEQ ID NO 19
<211> LENGTH: 20

<212> TYPE: DNA
<213> ORGANISM: Human

<400> SEQUENCE: 19
cactactaag gtaagtacct                                              20

<210> SEQ ID NO 20
<211> LENGTH: 20
<212> TYPE: DNA
<213> ORGANISM: Human

<400> SEQUENCE: 20
ctccccctag gtgtgtatga                                              20

<210> SEQ ID NO 21
<211> LENGTH: 20
<212> TYPE: DNA
<213> ORGANISM: Human

<400> SEQUENCE: 21
gccatatcag gtaactggca                                              20

<210> SEQ ID NO 22
<211> LENGTH: 20
<212> TYPE: DNA
<213> ORGANISM: Human

<400> SEQUENCE: 22
cgtgctgtag gaaaccattt                                              20

<210> SEQ ID NO 23
<211> LENGTH: 20
<212> TYPE: DNA
<213> ORGANISM: Human

<400> SEQUENCE: 23
actgcctatg gtaggtagtg                                              20

<210> SEQ ID NO 24
<211> LENGTH: 21
<212> TYPE: DNA
<213> ORGANISM: Human

<400> SEQUENCE: 24 ttttcccca gaaacaagtg t                                             21

<210> SEQ ID NO 25
<211> LENGTH: 20
<212> TYPE: DNA
<213> ORGANISM: Human

<400> SEQUENCE: 25
aactgtgcag gtaaggataa                                              20

<210> SEQ ID NO 26
<211> LENGTH: 20
<212> TYPE: DNA
<213> ORGANISM: Human

<400> SEQUENCE: 26
tctgtctcag ctgcaagtgt                                              20

<210> SEQ ID NO 27

-continued

```
<211> LENGTH: 20
<212> TYPE: DNA
<213> ORGANISM: Human

<400> SEQUENCE: 27
ccctttgaag gtattggaag                                              20

<210> SEQ ID NO 28
<211> LENGTH: 20
<212> TYPE: DNA
<213> ORGANISM: Human

<400> SEQUENCE: 28
acagaaagag gtctgtcctt                                              20

<210> SEQ ID NO 29
<211> LENGTH: 20
<212> TYPE: DNA
<213> ORGANISM: Human

<400> SEQUENCE: 29
ctctcgccag gaatcttaca                                              20

<210> SEQ ID NO 30
<211> LENGTH: 20
<212> TYPE: DNA
<213> ORGANISM: Human

<400> SEQUENCE: 30
gatctcattc atatcctttt                                              20

<210> SEQ ID NO 31
<211> LENGTH: 30
<212> TYPE: DNA
<213> ORGANISM: Human

<400> SEQUENCE: 31
ctccttaaca atgtgcccac agtctctcag                                   30

<210> SEQ ID NO 32
<211> LENGTH: 22
<212> TYPE: DNA
<213> ORGANISM: Artificial
<220> FEATURE:
<223> OTHER INFORMATION: PCR primer

<400> SEQUENCE: 32
aggcgcagaa ctggtaggta tg                                           22

<210> SEQ ID NO 33
<211> LENGTH: 23
<212> TYPE: DNA
<213> ORGANISM: Artificial
<220> FEATURE:
<223> OTHER INFORMATION: PCR primer

<400> SEQUENCE: 33
gctaaggatg gtttctagcg atg                                          23

<210> SEQ ID NO 34
<211> LENGTH: 24
<212> TYPE: DNA
<213> ORGANISM: Artificial
<220> FEATURE:
<223> OTHER INFORMATION: PCR primer
```

```
<400> SEQUENCE: 34
tactgttttt gcgatctgcc gttt                                          24

<210> SEQ ID NO 35
<211> LENGTH: 22
<212> TYPE: DNA
<213> ORGANISM: Artificial
<220> FEATURE:
<223> OTHER INFORMATION: PCR primer

<400> SEQUENCE: 35
aatacgactc actataggga ga                                            22

<210> SEQ ID NO 36
<211> LENGTH: 28
<212> TYPE: DNA
<213> ORGANISM: Artificial
<220> FEATURE:
<223> OTHER INFORMATION: PCR primer

<400> SEQUENCE: 36
acgttacaac aaagattaga agacctgg                                      28

<210> SEQ ID NO 37
<211> LENGTH: 24
<212> TYPE: DNA
<213> ORGANISM: Artificial
<220> FEATURE:
<223> OTHER INFORMATION: PCR primer

<400> SEQUENCE: 37
tgctgagtgg ccccacggcg caag                                          24

<210> SEQ ID NO 38
<211> LENGTH: 23
<212> TYPE: DNA
<213> ORGANISM: Artificial
<220> FEATURE:
<223> OTHER INFORMATION: PCR primer

<400> SEQUENCE: 38
ccatttctgg acggctaaag acc                                           23

<210> SEQ ID NO 39
<211> LENGTH: 23
<212> TYPE: DNA
<213> ORGANISM: Artificial
<220> FEATURE:
<223> OTHER INFORMATION: PCR primer

<400> SEQUENCE: 39
gcagacactt tggctaaggc ggc                                           23

<210> SEQ ID NO 40
<211> LENGTH: 20
<212> TYPE: DNA
<213> ORGANISM: Artificial
<220> FEATURE:
<223> OTHER INFORMATION: PCR primer

<400> SEQUENCE: 40
ccagagcgtg acatgcattc                                               20

<210> SEQ ID NO 41
```

```
<211> LENGTH: 28
<212> TYPE: DNA
<213> ORGANISM: Artificial
<220> FEATURE:
<223> OTHER INFORMATION: PCR primer

<400> SEQUENCE: 41
ccaggtcttc taatctttgt tgtaacgt                                              28

<210> SEQ ID NO 42
<211> LENGTH: 23
<212> TYPE: DNA
<213> ORGANISM: Artificial
<220> FEATURE:
<223> OTHER INFORMATION: PCR Primer

<400> SEQUENCE: 42
ggaagcttgt cgattgctta tcc                                                   23

<210> SEQ ID NO 43
<211> LENGTH: 26
<212> TYPE: DNA
<213> ORGANISM: Artificial
<220> FEATURE:
<223> OTHER INFORMATION: PCR Primer

<400> SEQUENCE: 43
agatcttcat catgactgtg gattgc                                                26

<210> SEQ ID NO 44
<211> LENGTH: 22
<212> TYPE: DNA
<213> ORGANISM: Artificial
<220> FEATURE:
<223> OTHER INFORMATION: PCR primer

<400> SEQUENCE: 44
agcaagttca gcctggttaa gt                                                    22

<210> SEQ ID NO 45
<211> LENGTH: 21
<212> TYPE: DNA
<213> ORGANISM: Artificial
<220> FEATURE:
<223> OTHER INFORMATION: PCR primer

<400> SEQUENCE: 45
gggaccttct ttatgagtat t                                                     21

<210> SEQ ID NO 46
<211> LENGTH: 30
<212> TYPE: DNA
<213> ORGANISM: Artificial
<220> FEATURE:
<223> OTHER INFORMATION: PCR primer

<400> SEQUENCE: 46
gaaggcacat ggctgaatat cgacggtttc                                            30

<210> SEQ ID NO 47
<211> LENGTH: 30
<212> TYPE: DNA
<213> ORGANISM: Artificial
<220> FEATURE:
<223> OTHER INFORMATION: PCR primer

<400> SEQUENCE: 47
```

-continued

```
gacaccagac caactggtaa tggtagcgac                              30

<210> SEQ ID NO 48
<211> LENGTH: 21
<212> TYPE: DNA
<213> ORGANISM: Human

<400> SEQUENCE: 48
tgatgggagg caacttttc t                                        21

<210> SEQ ID NO 49
<211> LENGTH: 30
<212> TYPE: DNA
<213> ORGANISM: Human

<400> SEQUENCE: 49
acacgtcatc atcctgtgaa ccattgaagt                              30

<210> SEQ ID NO 50
<211> LENGTH: 31
<212> TYPE: DNA
<213> ORGANISM: Human

<400> SEQUENCE: 50
atttttaaat gatactgaga tatcatgtaa a                            31

<210> SEQ ID NO 51
<211> LENGTH: 33
<212> TYPE: DNA
<213> ORGANISM: Human

<400> SEQUENCE: 51
atttttaaat gatactgaga tatcatgtat cag                          33

<210> SEQ ID NO 52
<211> LENGTH: 23
<212> TYPE: DNA
<213> ORGANISM: Human

<400> SEQUENCE: 52
tcatttcttc cctcatttat tca                                     23
```

GENE, DISRUPTED IN SCHIZOPHRENIA

FIELD OF THE INVENTION

The present invention relates to a newly identified DNA sequence which surrounds a breakpoint on chromosome 1 involved in a balanced t(1;11)(q42.1;q14.3) translocation as well as to a gene disrupted by this translocation event and its encoded proteins as well as to antibodies thereto and their use as a medicament. The invention also relates to methods for the detection of the translocation event as well as to methods for the in vitro diagnosis of a psychiatric disorder. Moreover, the invention also relates to transformed cell lines.

BACKGROUND OF THE INVENTION

Family, twin and adoption studies have convincingly demonstrated a significant genetic contribution to schizophrenia (1995, Lancet 346: 678-682, and references therein) and have driven studies directed at identification of this genetic component. Schizophrenia is a complex disease and the multifactorial and probable genetic heterogeneity of the condition complicates the application and interpretation of conventional linkage and association studies. At present, however, no specific genes have been described which could play a role in schizophrenia.

Previously, a balanced t(1;11)(q42.1;q14.3) translocation was reported which is linked to schizophrenia and other related mental illness in a large Scottish family (1990, Lancet 336: 13-16) with a maximum LOD of 6.0 (Douglas Blackwood, in preparation). Mapping of the translocation breakpoint on chromosome 11, and the accompanying search for neighbouring genes has already been reported (1997, Am. J. Med. Genet. 74: 82-90, 1998, Pyschiatr. Genet. 8: 175-181). No evidence for the presence of any part of a gene closer than 250 kb to the breakpoint has been found.

It will be clear that there is a great need for the elucidation of genes related to schizophrenia in order to unravel the various roles these genes may play in the disease process. A better knowledge of the genes involved in schizophrenia and the mechanism of action of their encoded proteins might help to create a better insight into the etiology of this psychiatric disorder and its underlying molecular mechanisms. This could eventually lead to improved therapy and better diagnostic procedures.

SUMMARY OF THE INVENTION

The present invention provides such a novel gene which is located on chromosome 1 and is directly disrupted by the translocation event. More specific, the present invention provides for a gene, tentatively called DIS1 (Disrupted In Schizophrenia) whose cDNA sequence is shown in SEQ ID NO:1. DIS1 is disrupted within an intron of the gene with the result that a proportion of the coding sequence has been translocated to chromosome 11.

DETAILED DESCRIPTION OF THE INVENTION

The protein encoded by DIS1 is predicted to have a globular N-terminal domain(s) and a helical C-terminal domain with the potential to interact with other proteins via formation of a coiled coil. The coiled-coil structure is present in several proteins (particularly microtubule binding proteins) which are involved in the development and functioning of the nervous system. The putative structure of DIS1 is therefore compatible with a role in the nervous system.

DIS1 consists of 13 exons which we estimate to extend across at least 300 kb of genomic DNA. The translocation breakpoint lies within intron 8 of this gene. The effect of the translocation is therefore to remove exons 9-13 to chromosome 11. There is a commonly used alternative splice site, which does not disrupt the open reading frame, within exon 11 which give rise to two distinct polypeptides as provided in SEQ ID NO: 2 and SEQ ID NO: 3. Table 1 shows the nucleotide sequences of the splice sites. The sequence of intron 8 is now revealed I SEQ ID NO: 4. At nucleotide 8432 a gap of unknown size occurs in the sequence.

The density of genes in the chromosome 1 breakpoint region is apparently high since, in addition to DIS1, 8 independent ESTs have also been identified. While this may suggest the presence of other genes in the region, it is also possible that some of these ESTs represent differentially spliced exons of DIS1.

TABLE 1

DIS1 splice site sequences

| exon | exon size | position | splice acceptor | splice donor |
|---|---|---|---|---|
| 1 | 120 bp | 1-120 | N/A | CACCGCGCAGgtaggggagc SEQ ID NO:7 |
| 2 | 980 bp | 121-1100 | ttcttcccagGCAGCCGGGA SEQ ID NO:8 | GCAGATGGAGgtcagtgtct SEQ ID NO:9 |
| 3 | 70 bp | 1101-1170 | accaacatagGTAATATCCT SEQ ID NO:10 | TATGATAAAGgtgagttta SEQ ID NO:11 |
| 4 | 151 bp | 1171-1321 | gggcttccagCTGAGACGTT SEQ ID NO:12 | CCACTCAGCAgtgaatacct SEQ ID NO:13 |
| 5 | 130 bp | 1322-1451 | ttgttttaagGGCCAGCGGA SEQ ID NO:14 | GCAGCTACAGgtgagcaggt SEQ ID NO:15 |
| 6 | 236 bp | 1452-1687 | ttctctacagAAAGAAATTG SEQ ID NO:16 | CCATAAGGAGgtactgctga 1 SEQ ID NO:17 |

TABLE 1-continued

DIS1 splice site sequences

| exon | exon size | position | splice acceptor | splice donor |
|---|---|---|---|---|
| 7 | 55 bp | 1688-1742 | attcttccagCCTCCAGGAA SEQ ID NO:18 | CACTACTAAGgtaagtacct SEQ ID NO:19 |
| 8 | 103 bp | 1743-1845 | ctccccctagGTGTGTATGA SEQ ID NO:20 | GCCATATCAGgtaactggca 1 SEQ ID NO:21 |
| 9 | 189 bp | 1846-2034 | cgtgctgtagCAAACCATTT SEQ ID NO:22 | ACTGCCTATGgtaggtagtg SEQ ID NO:23 |
| 10 | 61 bp | 2035-2095 | ttttcccccagAAACAAGTGT SEQ ID NO:24 | AACTGTGCAGgtaaggataa 1 SEQ ID NO:25 |
| 11a | 199 bp | 2096-2294 | tctgtctcagCTGCAAGTGT SEQ ID NO:26 | CCCTTTGAAGgtattggaag SEQ ID NO:27 |
| 11b | 265 bp | 2096-2360 | tctgtctcagCTGCAAGTGT SEQ ID NO:26 | ACAGAAAGAGgtctgtcctt SEQ ID NO:28 |
| 12 | 118 bp | 2361-2478 | ctctcgccagGAATCTTACA SEQ ID NO:29 | GATCTCATTCatatcctttt 1 SEQ ID NO:30 |
| 13 | 4430-4585* | 2479-6913 | ctccttaacaatgtgcccacAGTCTCTCAG SEQ ID NO:31 | N/A |

*Exon size depends upon poly(A) signal usage and poly(A) addition site selection DIS1 is predicted to encode a protein with an N-terminal globular head consisting mainly of beta-sheet, and solvent-exposed helical tail with the potential to form coiled-coils. The transition from beta-sheet to alpha-helix occurs essentially at the boundary between exons 2 and 3. Exons 1 and 2 therefore encode the putative globular domain(s), while exons 3 to 13 encode the putative helical tail of DIS1.

We propose that DIS1 should be considered as candidate gene involved in the aetiology of psychiatric disorders because it is directly disrupted by the translocation. In support of this contention is the predicted structure of DIS1, which is compatible with a role in development and functioning of the nervous system. The information contained herein, now enables the skilled person to assess the gene as candidate in psychotic individuals unrelated to members of the family carrying the translocation. This is particularly important given that our mapping of the chromosome 1 breakpoint region has identified several ESTs which indicates the possible presence of additional genes. Even if such genes are not directly disrupted by the translocation, positional effects on their expression cannot be ruled out. Determination of the genomic structure of DIS1 has provided the information required to look for mutations in all of the transcribed sequence plus splice sites and DIS1 can now be evaluated by means of mutation screening and association studies.

The sequences of the present invention can be used to derive primers and probes for use in DNA amplification reactions in order to perform diagnostic procedures or to identify further, neighbouring genes which also may contribute to the development of schizophrenia.

It is known in the art that genes may vary within and among species with respect to their nucleotide sequence. The DIS1 genes from other species may be readily identified using the above probes and primers. Therefore, the invention also comprises functional equivalents, which are characterised in that they are capable of hybridising to at least part of the DIS1 sequence shown in SEQ ID NO: 1, preferably under high stringency conditions.

Two nucleic acid fragments are considered to have hybridisable sequences if they are capable to hybridising to one another under typical hybridisation and wash conditions, as described, for example in Maniatis, et al., pages 320-328, and 382-389, or using reduced stringency wash conditions that allow at most about 25-30% basepair mismatches, for example: 2×SSC, 0.1% SDS, room temperature twice, 30 minutes each, then 2×SSC, 0.1% SDS 37° C. once, 30 minutes; then 2×SSC, room temperature twice ten minutes each. Preferably, homologous nucleic acid strands contain 15-25% basepair mismatches, even more preferably 5-15% basepair mismatches. These degrees of homology can be selected by using wash conditions of appropriate stringency for identification of clones from gene libraries or other sources of genetic material, as is well known in the art.

Furthermore, to accommodate codon variability, the invention also includes sequences coding for the same amino acid sequences as the sequences disclosed herein. Also portions of the coding sequences coding for individual domains of the expressed protein are part of the invention as well as allelic and species variations thereof. Sometimes, a gene expresses different isoforms in a certain tissue which includes splicing variants, that may result in an altered 5' or 3' mRNA or in the inclusion of an additional exon sequence. Alternatively, the messenger might have an exon less as compared to its counterpart as exemplified in the sequences enlisted here (SEQ ID NO: 3 contains an additional 22 amino acids as compared to SEQ ID NO 2 due to an alternative splicing event). These sequences as well as the proteins encoded by these sequences all are expected to perform the same or similar functions and form also part of the invention.

The sequence information as provided herein should not be so narrowly construed as to require inclusion of erroneously identified bases. The specific sequence disclosed herein can be readily used to isolate further genes which in turn can easily be subjected to further sequence analyses thereby identifying sequencing errors. Thus, in one aspect, the present invention provides for isolated polynucleotides encoding a novel gene, disrupted in schizophrenia.

The DNA according to the invention may be obtained from cDNA. Alternatively, the coding sequence might be genomic DNA, or prepared using DNA synthesis techniques. The polynucleotide may also be in the form of RNA. The polynucleotide may be in single stranded or double stranded form. The single strand might be the coding strand or the non-coding (anti-sense) strand.

The present invention further relates to polynucleotides which have at least 80%, preferably 90% and more preferably 95% and even more preferably at least 98% identity with SEQ ID NO:1. Such polynucleotides encode polypeptides which retain the same biological function or activity as the natural, mature protein.

The percentage of identity between two sequences can be determined with programs such as DNAMAN (Lynnon Biosoft, version 3.2). Using this program two sequences can be aligned using the optimal alignment algorithm of Smith and Waterman (1981, J. Mol. Biol, 147:195-197). After alignment of the two sequences the percentage identity can be calculated by dividing the number of identical nucleotides between the two sequences by the length of the aligned sequences minus the length of all gaps.

The DNA according to the invention will be very useful for in vivo or in vitro expression of the novel gene according to the invention in sufficient quantities and in substantially pure form.

In another aspect of the invention, there are provided polypeptides comprising the amino acid sequence encoded by the above described DNA molecules.

Preferably, the polypeptides according to the invention comprise at least part of the amino acid sequences as shown in SEQ ID NO:2 and SEQ ID NO:3.

Also functional equivalents, that is polypeptides homologous to SEQ ID NO: 2 or SEQ ID NO: 3 or parts thereof having variations of the sequence while still maintaining functional characteristics, are included in the invention.

The variations that can occur in a sequence may be demonstrated by (an) amino acid difference(s) in the overall sequence or by deletions, substitutions, insertions, inversions or additions of (an) amino acid(s) in said sequence. Amino acid substitutions that are expected not to essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science, 1985, 227, 1435-1441) and determining the functional similarity between homologous polypeptides. It will be clear that also polynucleotides coding for such variants are part of the invention.

The polypeptides according to the present invention include the polypeptides comprising SEQ ID NO:2 and SEQ ID NO:3 but also their isoforms, i.e. polypeptides with a similarity of 70%, preferably 90%, more preferably 95%. Also portions of such polypeptides still capable of conferring biological effects are included. Especially portions which still bind to ligands form part of the invention. Such portions may be functional per se, e.g. in solubilized form or they might be linked to other polypeptides, either by known biotechnological ways or by chemical synthesis, to obtain chimeric proteins. Such proteins might be useful as therapeutic agent in that they may substitute the gene product in individuals with abberant expression of the DIS1 gene.

The sequence of the gene may also be used in the preparation of vector molecules for the expression of the encoded protein in suitable host cells. A wide variety of host cell and cloning vehicle combinations may be usefully employed in cloning the nucleic acid sequence coding for the DIS1 gene of the invention or parts thereof. For example, useful cloning vehicles may include chromosomal, non-chromosomal and synthetic DNA sequences such as various known bacterial plasmids and wider host range plasmids and vectors derived from combinations of plasmids and phage or virus DNA.

Vehicles for use in expression of the genes or a ligand-binding domain thereof of the present invention will further comprise control sequences operably linked to the nucleic acid sequence coding for a ligand-binding domain. Such control sequences generally comprise a promoter sequence and sequences which regulate and/or enhance expression levels. Of course control and other sequences can vary depending on the host cell selected.

Suitable expression vectors are for example bacterial or yeast plasmids, wide host range plasmids and vectors derived from combinations of plasmid and phage or virus DNA. Vectors derived from chromosomal DNA are also included. Furthermore an origin of replication and/or a dominant selection marker can be present in the vector according to the invention. The vectors according to the invention are suitable for transforming a host cell.

Recombinant expression vectors comprising the DNA of the invention as well as cells transformed with said DNA or said expression vector also form part of the present invention.

Suitable host cells according to the invention are bacterial host cells, yeast and other fungi, plant or animal host such as Chinese Hamster Ovary cells or monkey cells. Thus, a host cell which comprises the DNA or expression vector according to the invention is also within the scope of the invention. The engineered host cells can be cultured in conventional nutrient media which can be modified e.g. for appropriate selection, amplification or induction of transcription. The culture conditions such as temperature, pH, nutrients etc. are well known to those ordinary skilled in the art.

The techniques for the preparation of the DNA or the vector according to the invention as well as the transformation or transfection of a host cell with said DNA or vector are standard and well known in the art, see for instance Sambrook et al., *Molecular Cloning: A laboratory Manual. 2$^{nd}$ Ed.*, Cold Spring Harbor Laboratory, Cold Spring Harbor, N.Y., 1989.

The proteins according to the invention can be recovered and purified from recombinant cell cultures by common biochemical purification methods including ammonium sulfate precipitation, extraction, chromatography such as hydrophobic interaction chromatography, cation or anion exchange chromatography or affinity chromatography and high performance liquid chromatography. If necessary, also protein refolding steps can be included.

DIS1 gene products according to the present invention can be used for the in vivo or in vitro identification of novel ligands or analogs thereof. For this purpose binding studies can be performed with cells transformed with DNA according to the invention or an expression vector comprising DNA according to the invention, said cells expressing the DIS1 gene products according to the invention.

Alternatively also the DIS1 gene products according to the invention as well as ligand-binding domains thereof can be used in an assay for the identification of functional ligands or analogs for the DIS1 gene products.

Methods to determine binding to expressed gene products as well as in vitro and in vivo assays to determine biological activity of gene products are well known. In general, expressed gene product is contacted with the compound to be tested and binding, stimulation or inhibition of a functional response is measured.

Thus, the present invention provides for a method for identifying ligands for DIS1 gene products, said method comprising the steps of:
a) introducing into a suitable host cell a polynucleotide according to the invention,
b) culturing cells under conditions to allow expression of the DNA sequence
c) optionally isolating the expression product
d) bringing the expression product (or the host cell from step b)) into contact with potential ligands which will possibly bind to the protein encoded by said DNA from step a);
e) establishing whether a ligand has bound to the expressed protein.
f) Optionally isolating and identifying the ligand As a preferred way of detecting the binding of the ligand to the expressed protein, also signal transduction capacity may be measured.

The present invention thus provides for a quick and economic method to screen for therapeutic agents for the prevention and/or treatment of diseases related to schizophrenia. The method is especially suited to be used for the high throughput screening of numerous potential compounds.

Compounds which activate or inhibit the function of DIS1 gene products may be employed in therapeutic treatments to activate or inhibit the polypeptides of the present invention.

Also within the scope of the invention are antibodies, especially monoclonal antibodies raised against the polypeptide molecule according to the invention. Such antibodies can be used therapeutically to inhibit DIS1 gene product function and diagnostically to detect DIS1 gene products.

The invention furthermore relates to the use of the DIS1 gene products as part of a diagnostic assay for detecting psychiatric abnormalities or susceptibility to psychiatric disorders related to mutations in the nucleic acid sequences encoding the DIS1 gene. Such mutations may e.g. be detected by using PCR (Saiki et al., 1986, Nature, 324, 163-166). Also the relative levels of RNA can be determined using e.g. hybridization or quantitative PCR technology. The presence and the levels of the DIS1 gene products themselves can be assayed by immunological technologies such as radioimmuno assays, Western blots and ELISA using specific antibodies raised against the gene products. Such techniques for measuring RNA and protein levels are well known to the skilled artisan.

The determination of expression levels of the DIS1 gene products in individual patients may lead to fine tuning of treatment protocols.

Also, transgenic animals may be prepared in which the expression of the DIS1 gene is altered or abolished.

LEGENDS TO THE FIGURES

FIG. 1 Alignment of sequence immediately flanking the breakpoints from the normal chromosome 1, der (1), der (11) and normal chromosome 11 (wt1, der (1), der (11) and wt11 respectively).

FIG. 2 Map of the chromosome 1 breakpoint region containing DIS1. Black boxes, DIS1 exons; Letters marking vertical arrows, position of ESTs. Positions of the putative CpG island, putative translation start and stop sites, polyadenylation signals and alternative splice site are indicated. EST accession numbers: A=AA777274, B=AA361879, C=AA311762, D=Hs.96883, E=AA249072, F=W04811, G=D78808, H=N49833, I=W29023/AA093172, J&K=H71071/Z40262, M=AA610789, 13=Hs.26985. ESTs J and K are located extremely close together such that their order could not be determined.

EXAMPLES

Example 1

Cloning of the Chromosome 1 Translocation Breakpoint

We have previously described the isolation of a 2.5 kb EcoRI fragment (wt11) containing the normal chromosome 11 translocation breakpoint, and demonstrated that it hybridises to EcoRI fragments of 2.7 kb and 7 kb from the der (1) and der (11) chromosomes respectively (1998, Psychiatr. Genet. 8: 175-181). This chromosome 11 breakpoint fragment was subcloned, and used to prepare a 2.15 kb HindIII/EcoRI repeat-free sub-fragment with which an EcoRI total digest genomic library made from a cell line from a translocation carrier (MAFLI, 1993, Am. J. Hum. Genet. 52: 478-490) was screened. A 2.7 kb EcoRI fragment, presumed to correspond to the der (1) translocation fragment was obtained. This was confirmed by its hybridisation pattern (FIG. 1), where it hybridises to a 2.7 kb fragment from MIS7.4, a hybrid cell line carrying the der (1) chromosome as its human component (1998, Psychiatr. Genet. 8: 175-181). Three fragments are visible from MAFLI; the 2.5 kb wild-type 11 breakpoint fragment; the 2.7 kb der (1) fragment and a fragment of 7.3 kb, assumed to be the wild-type chromosome 1 breakpoint fragment. This was confirmed using normal control human DNA which also shows hybridisation of the probe to the 2.5 kb chromosome 11 breakpoint fragment, and to a 7.3 kb fragment which must therefore be from chromosome 1.

The 2.7 kb der (1) fragment was used to rescreen the library, avoiding any clones which had previously hybridised to the chromosome 11 breakpoint fragment, and this yielded a 7.3 kb clone (wt1), corresponding to the chromosome 1 breakpoint fragment.

Example 2

Identification of the Breakpoint

The cloned wt11, wt1 and der (1) fragments were sequenced and the positions of the translocation breakpoints were identified by comparisons between these three sequences. Primers designed from wt11 and wt1 sequence amplified a 1.4 kb fragment containing the breakpoint from the der (11) chromosome by PCR, and the product was partially sequenced. An alignment of the breakpoint sequences from each of the four chromosomes is presented in FIG. 1. This shows that the translocation event resulted in no rearrangement at all on the der (1) chromosome, and a small rearrangement on the der (11), where there has been a deletion of the nucleotides TCAG accompanied by insertion of M. This breakpoint sequence and minor rearrangement has been confirmed by genomic sequence analysis of two other translocation carriers (data not shown). The position of the breakpoint has also been confirmed using pairs of primers, one primer pair from each side of the breakpoint, for PCR on genomic DNA from MIS7.4 and MIS39, cell lines carrying the der (1) and der (11) chromosomes respectively (data not shown).

Example 3

Breakpoint Sequence Analysis

The sequences of the breakpoint fragments from chromosomes 1 and 11 were used to search sequence databases using BLAST (1997, Nucleic Acids. Res. 25: 3389-3402) to identify matches indicating the presence of a gene, and also analysed using the suite of gene recognition and analysis programmes encompassed by Nucleotide Identify X (NIX, menu.hgmp.mrc.ac.uk/menu-bin/Nix/Nix.pl).

BLAST searches of sequence databases identified sequence from one end of a BAC clone (Genbank/EMBL accession number AQ105798) within the wt11 fragment, but nothing else of note. Neither did NIX convincingly predict any exons to be present within the chromosome 11 breakpoint sequence. However the wt1 fragment contains several interesting sequences. There is a tandemly repeated TAA trinucleotide which is contained within three overlapping sequence tagged sites (Genbank/EMBL accession numbers G09671, G09453 and G07779). These correspond to the marker D1S1621, which maps approximately 120 bp below the breakpoint. There are also sequence matches to the ends of three different BAC clones (Genbank/EMBL accession numbers AQ112950, AQ078498 and B40542).

From Genbank and EMBL, sequence matches to three separate expressed sequence tags (ESTs), and a messenger RNA, are also contained within the wt1 fragment, all distal to the breakpoint. These are AA249072 (which overlaps with D1S1621), W04811, D78808 and AB007926, mapping approximately 80 bp, 1.8 kb, 2.8 kb and 3.7 kb from the breakpoint respectively (FIG. 2).

Homology to AA249072 and WO4811 extends across the whole sequence obtained from each cDNA. However sequence corresponding to wt1 in D78808 could be spurious. Only 103 nulceotides of the total 350 in the EST sequence are contained within the wt1 sequence, yet this short match does not apparently correspond to an exon since there are not flanking splice sites. The remaining sequence is homologous to several other ESTs (UniGene cluster Hs.31446, www.ncbi.nlm.nih.gov/UniGene/index.html), none of which contain any wt1 sequence or are even present on chromosome 1, as judged by a lack of hybridization to genomic DNA from the chromosome 1 human/mouse hybrid cell line A9(Neo-1)-4 (data not shown). AB007926 consists of 6833 nucleotides of a brain-expressed transcript from chromosome 1 (1997, DNA Res. 4:345-349). Only 189 nucleotides of this transcript are coincident with wt1.

NIX identified one putative exon with consensus splice sites on the forward strand of wt1. This exon contains all of the sequence match to mRNA AB007926. The match ends at the predicted splice sites, demonstrating the accuracy of the prediction.

Example 4

Contig Construction

Genomic clones from the region were isolated from a PAC library, RPCI1 (1996, Construction of bacterial artificial chromosome libraries using the modified P1 (PAC) System. In "Current Protocols in Human Genetics", N. C. Dracopoli, J. L. Haines, B. R. Korf, D. T. Moir, C. C. Morton, C. E. Seidman, J. G. Seidman and D. R. Smith, Eds., Unit 5.15 Pub. John Wiley and Sons, New York) distributed by the United Kingdom Human Genome Mapping Project Resource Centre, and a chromosome 1 cosmid library, provided by the Resource Centre of the German Human Genome Project at the Max-Planck-Institute for Molecular Genetics (1994, Nature, 367: 489-491, 1999, Nature Genetics, 22: 22). Contig construction essentially required three phases. Initially, genomic clones were identified by screening libraries with sequence flanking the breakpoint, microdissection clone MD258 (1995, Cytogenet. Cell Genet. 70: 35-40), or with several cDNA fragments from DIS1. Overlaps between the clones were then determined by end sequencing using oligonucleotides bordering the cosmid and PAC vector cloning sites (data not shown). Pairs of primers were designed from the resulting sequence and overlapping clones were identified by PCR (data not shown). For verification, the PCR products were hybridised to Southern blots of digested PAC and cosmid DNA (data not shown). Finally, remaining gaps in the contig were filled by further rounds of library screening using PCR products generated from clone ends. In addition, cosmid ICRFc112B0519Q6 was used to screen the PAC library to extend the contig in the proximal direction. Two markers, D1S251 and D1S1621, have been mapped on this contig. D1S251 was mapped by PCR, while the location of D1S1621 immediately distal to the breakpoint was determined by genomic sequencing. The locations of DIS1 exons 1-3 and 5-13 and of all the ESTs with respect to the cosmids and PACs were determined by hybridisation of oligonucleotides (not shown) to digested cosmid and PAC DNA. ESTs 10 and 11 are located extremely close together such that their order with respect to the contig could not be determined by hybridisation. DIS1 exon 4 is known to be present in cosmid ICRFc112D2299QD4, but was not otherwise mapped because of the apparent presence of numerous related sequences in the surrounding DNA.

Example 5

A Contig Spanning the Chromosome 1 Translocation Breakpoint

To investigate the genomic structure of DIS1 we first constructed a contiguous clone map spanning the chromosome 1 breakpoint (FIG. 1). This contig is estimated to extend across at least 400 kb based on average PAC and cosmid sizes of 130 kb and 35 kb respectively. Cosmid fluorescence in situ hybridisation to the translocation cell line MAFLI was employed to confirm the orientation of the contig, and that it crosses the translocation breakpoint. Cosmids spanning the breakpoint, and located distal and proximal were found to hybridise as predicted. Cosmid ICRFc112I0142Q6 hybridises to the normal chromosome 1, and the derived 1 and derived 11 chromosomes, indicating that it crosses the breakpoint. Hybridisation of cosmid ICRFc112D1274QD4 to the normal chromosome 1 and derived 1, shows that it is located proximal to the breakpoint. Finally, signal from cosmid ICRFc112G1395QD4 is visible on the normal chromosome 1 and the derived chromosome 11 demonstrating that this cosmid lies distal to the breakpoint.

Example 6

Genomic Structure of DIS1

Direct cosmid sequencing using primers designed from DIS1 cDNA sequence was used to determine the intron/exon structure of DIS1. Resulting genomic sequence was aligned with cDNA sequence and splice sites identified at the points of divergence (table 1). Exons 1-3 and 5-13 were identified by this method. For technical reasons, exon 4 proved more difficult and splice site sequences were eventually identified by subcloning a genomic fragment containing the exon from a cosmid, followed by sequencing.

DIS1 consists of 13 exons extending across at least 300 kb of genomic DNA (FIG. 1). A region of 66 nucleotides which is deleted from some DIS1 transcripts was found to arise from utilisation of an internal splice donor site within exon 11 and the normal splice acceptor site of the same exon. The final intron of DIS1 is a member of the extremely rare AT-AC class of introns (1997, Trends. Biochem. Sci. 22:132-137). This intron has the consensus 5' and 3' splice site sequences, atatcctt and yccac respectively, as well as the consensus branch-site element, tccttaac, close to the 3' splice site as shown in table 1. All the other introns are of the common class I type.

Example 7

Mapping of Additional Transcribed Sequences in the Region

During contig construction, all of the sequences generated from the ends of the PACs and cosmids, miscellaneous sequences and the sequence of ICRFc112I0142Q6, were used to screen Genbank and EMBL in search of homologies to expressed sequence tags (ESTs). The locations of the 8 ESTs identified by database screening are shown (FIG. 1). Unigene cluster Hs.26985 (13) is derived from the 3' UTR of DIS1, while the remaining 8 ESTs have not yet been assigned to any known gene.

Example 8

Expression of DIS1

When hybridised to Northern blots, DIS1 was found to be present in all adult human tissues examined, as a transcript of approximately 8.1 kb. Various smaller transcripts hybridise to the same probe. Although these may represent DIS1 splice variants, their significance is not yet known. In agreement with the Northern blot data, RT-PCR using primers towards the 5' end of DIS1 on a range of human foetal tissues also detected transcripts in every tissue tested (table 2).

TABLE 2

RT-PCR analysis of DIS1 on a range of human foetal tissues. Approximate ages of gestation are given in weeks. 2: two bands obtained using one primer pair, +: transcript detected.

| Sample | age (weeks) | DIS1 proximal | DIS1 distal |
| --- | --- | --- | --- |
| brain | 8.3 | + | +(2) |
|  | 10.3 | + | +(2) |
|  | 13.3 | + | +(2) |
| heart | 8.0 | + | +(2) |
|  | 8.8 | + | +(2) |
|  | 9.1 | + | +(2) |
|  | 9.3 | + | +(2) |
| liver | 10.6 | + | +(2) |
| kidney | 10.0 | + | +(2) |
| spleen | 14.8 | + | +(2) |
| limb | 10.3 | + | +(2) |

Example 9

Tissue-Specific Distribution of DIS1

Analysis of DIS1 expression indicates that the gene is widely expressed in foetal tissues, and that DIS1 transcripts are present in all adult tissues examined. However, as well as normal functioning, it is also necessary to study what effect the translocation may have had on overall expression of the gene. DIS1 is disrupted within the open reading frame which may cause (1) production of a truncated transcript and protein retaining only one of the putative leucine zippers, (2) silencing of the disrupted allele, or (3) production of a fusion transcript/protein from a gene on chromosome 11.

Example 10

Cell Culture

The lymphoblastoid cell line MAFLI from an individual bearing the t(1;11)(q42.1;q14.3) translocation, somatic cell hybrids MIS7.4 and MIS39 bearing the der (1) or der (11) translocation chromosomes respectively, and their culture conditions, have been described previously (1993, Am. J. Hum. Genet. 52: 478-490). Der (1) refers to the derived chromosome 1 where DNA from 1q42.1-qter has been lost and replaced with chromosome 11 material from 11q14.3-qter. Der (11) refers to the reciprocal derived chromosome 11. The cell line A9(Neo-1)-4, a mouse A9 hybrid cell line carrying human chromosome 1, and its culture requirements, have been previously reported (1989, Jpn. J. Cancer Res., 80: 413-418).

Example 11

PCR Analysis of the Breakpoint Region of DIS1

A 1.4 kb product was amplified from the der 11 chromosome using one primer specific for chromosome 11 proximal to the breakpoint (ggctggatattgcccttgagccataatt, SEQ ID NO: 5) and one primer specific for chromosome 1 distal to the breakpoint (agaacagaggagggacgatgatgac, SEQ ID NO: 6). This product was obtained using the cell line MIS39 which carries the der 11 chromosome. This product is only obtainable from the translocated chromosome.

Example 12

FISH Analysis of the Breakpoint Region of DIS1

Cosmid fluorescence in situ hybridisation to the translocation cell line MAFLI was employed to confirm that the contig crosses the translocation breakpoint. Cosmid ICRFc112I0142Q6 hybridises to the normal chromosome 1, and the derived 1 and derived 11 chromosomes, indicating that it crosses the breakpoint.

Example 13

Methods

Fluorescence in Situ Hybridisation

Cosmids were mapped in relation to the chromosome 1 breakpoint using 2-7 day old slides of metaphase chromosomes prepared from the translocation cell line MAFLI by conventional methods. Cosmid DNA was labelled with dUTP-biotin by standard nick translation. FISH was carried out essentially as previously described (1995, Genomics 28: 420-428). Slides were examined on a Leitz microscope and suitable metaphases scanned with a BioRad MRC-600 confocal laser scanning system.

DNA Preparation

Cosmid and PAC DNA was prepared by standard methods (Sambrook et al., *Molecular Cloning: A laboratory Manual.* 2$^{nd}$ Ed., Cold Spring Harbor Laboratory, Cold Spring Harbor, N.Y., 1989).

Prior to sequencing, cosmid and PAC DNA was subjected to a phenol/chloroform clean-up step, followed by ethanol precipitation. Alternatively, cosmid DNA was prepared using Qiagen plasmid midi kits, followed by dialysis. Cosmid DNA prepared for sequencing was stored at 4° C. Plasmid DNA was prepared using QIAGEN plasmid midi kits.

DNA Sequencing

Cosmid end sequencing was carried out using primers 928 (aggcgcagaactggtaggtatg, SEQ ID NO: 32) and 929 (gctaaggatggtttctagcgatg, SEQ ID NO: 33). PAC sequencing was carried out using primers SP6 (tactgttttgcgatctgccgttt, SEQ ID NO: 34) and T7 (aatacgactcactatagggaga, SEQ ID NO: 35). For cosmids and PACs 0.5-1 microgrammes of DNA was sequenced using ABI PRISM Big Dye terminator cycle sequencing ready reaction kits with 60 ng of primer. Plasmid DNA sequencing reactions were performed using ABI PRISM dRhodamine terminator cycle sequencing ready reaction kits and the products separated on an ABI 377 DNA sequencer (PE Applied Biosystems), according to the manufacturers instructions. Resulting sequence was analysed using the GCG package of sequence analysis software (Wisconsin package version 9.1, Genetics Computer Group, Madison, Wis.). BLAST (1997, Nucleic. Acids. Res. 25: 3389-3402) searches were carried out at the National Center for Biotechnology Information (www.ncbi.nlm.nih.gov).

RNA Extraction and cDNA Synthesis

Human foetal tissues were obtained from the Medical Research Council Tissue Bank. Total RNA was extracted using RNazol B™ (Biogenesis Ltd.) according to the manufacturers instructions. First strand cDNA synthesis was carried out on DNAse I treated RNA using the random hexamer primer from the SUPERSCRIPT™ Preamplification System (GIBCO BRL) according to the manufacturers instructions. 1 microlitre of the resulting cDNA was used in standard PCR reactions.

Subcloning the Chromosome 11 Breakpoint Fragment

The 2.5 kb EcoRI fragment isolated as described previously (1998, Psychiatr. Genet. 8: 175-181) was cloned into EcoRI-digested pBluescript SK (−) (Stratagene) using standard methods (Sambrook et al., *Molecular Cloning: A laboratory Manual.* 2nd Ed., Cold Spring Harbor Laboratory, Cold Spring Harbor, N.Y., 1989).

Genomic Library Construction and Screening

Genomic DNA from the translocation cell line MAFLI was digested with EcoRI, ligated into EcoRI-digested and dephosphorylated lambda ZAP II (Stratagene), and packaged using Gigapack Gold II packaging extract (Stratagene) according to the manufacturers instructions. Bacteriophage were plated using *E. coli* XL1-Blue MRF' and the library of clones screened using standard methods. Excision of clones from the lambda vector was carried out as advised by the manufacturer, releasing genomic fragments cloned into pBluescript SK (−). The library was screened using the 2.15 kb repeat-free HindIII/EcoRI fragment containing the chromosome 11 breakpoint, followed by the 2.7 kb der (1) fragment. Of 1×10$^7$ clones screened, one copy of the 2.5 kb chromosome 11 fragment, four copies of the 2.7 kb der (1) fragment, one copy of the 7.3 kb chromosome 1 fragment and no copies of the 7 kb der (11) fragment were obtained.

cDNA Library Screening 20-26 week foetal brain and 20-25 week foetal heart 5'-STRETCH PLUS cDNA libraries, constructed in lambda gt10 and gt11 respectively, were obtained from Clontech and screened according to the manufacturers instructions. Inserts were obtained from pure clones using two methods. Firstly, cDNAs were amplified by PCR, turbocloned (1993, Nucleic Acids Res. 21: 817-821) and sequenced. Due to the probable introduction of sequence alterations during PCR, several subclones were sequenced. Alternatively, lambda DNA was digested with EcoRI to release the cDNA insert which was then subcloned into EcoRI-digested pBluescript SK (−) (Stratagene).

Polymerase Chain Reactions

PCR was carried out using AmpliTaq DNA polymerase (Perkin Elmer). Each 50 microliter reaction contained 1 unit of enzyme, 300 ng of each primer, 200 mM of each dNTP, 1.5 mM MgCl$_2$, 50 mM KCI and 10 mM Tris-HCl pH 8.3. A probe corresponding to nucleotides 1177-1321 of DIS1 was prepared from cloned cDNA using primers ACGTTACAACAAAGATTAGAAGACCTGG (SEQ ID NO: 36) and TGCTGAGTGGCCCCACGGCGCAAG (SEQ ID NO: 37), with touchdown PCR (75° C.-65° C.) and 30s denaturation at 94° C., 30s synthesis at 72° C. Marker DIS251 was mapped by PCR using the standard cycling conditions for this marker.

A probe containing the DIS1 exon predicted by NIX was prepared by PCR using the wt1 fragment as template and primers CCATTTCTGGACGGCTAAAGACC (SEQ ID NO: 38) & GCARACACTTTGGCTAAGGCGGC (SEQ ID NO: 39) (694 bp product). The cycling conditions used were: 35 cycles of: 94° C., 30s; 58° C., 60s; 72° C., 60s. Amplification from DIS1 cDNA was performed using proximal primers CCAGAGCGTGACATGCATTC (SEQ ID NO: 40) & CCAGGTCTTCTAATCTTTGTTGTAACGT (SEQ ID NO: 41) (292 bp product from 35 cycles of: 94° C., 30s; 62° C., 60s; 72° C., 30s) and distal primers GGAAGCTTGTCGATTGCTTATCC (SEQ ID NO: 42) & AGATCTTCATCATGACTGTGGATTGC (SEQ ID NO: 43) (270 & 336 bp products from 35 cycles of: 94° C., 30s; 64° C., 60s; 72° C., 30s). An initial hot start step was carried out. This involved preparation of two separate mixes, one containing template, buffer and nucleotides, and the other containing enzyme and primers. These were incubated at 90° C. separately for two minutes prior to mixing and cycling.

In order to amplify cDNA inserts from lambda vectors, a single plaque was picked into 25 microliters of distilled water. 1-5 microliters were then added to a PCR reaction and the cDNA insert amplified using vector-based primers. Lambda gt10-specific primers, AGCAAGTTCAGCCTGGTTAAGT (SEQ ID NO: 44) & GGGACCTTCTTTATGAGTATT (SEQ ID NO: 45) (35 cycles of: 94° C., 30s; 68VC, 60s; 72° C., 180s) and lambda gt11-specific primers GAAGGCACATGGCTGAATATCGACGGTTTC (SEQ ID NO: 46) & GACACCAGACCAACTGGTAATGGTAGCGAC (SEQ ID NO: 47) (35 cycles of 94° C., 30s; 56° C., 60s; 72° C., 90s) were used to amplify inserts from the foetal brain and foetal heart cDNA libraries respectively.

Hybridisation

Standard procedures were used for Southern blotting and hybridisation (Sambrook et al., *Molecular Cloning: A laboratory Manual.* 2nd Ed., Cold Spring Harbor Laboratory, Cold Spring Harbor, N.Y., 1989). Probes were labelled with alpha $^{32}$P-dCTP by random priming using High Prime (Boehringer Mannheim) and purified using Pharmacia NICK columns. The oligonucleotide probe was labelled with gamma $^{32}$P-dATP. Oligonucleotide hybridisations were carried out overnight at the appropriate temperature.

Subcloning

Exon 4 of DIS1 (and flanking DNA) was subcloned from cosmid ICRFc112D2299QD4 by digestion with EcoRI. Digested fragments were subcloned into EcoRI-digested pBluescript SK (−) (Sratagene) and subclones containing the exon were identified by hybridisation with the DIS1 cDNA nucleotide 1177-1321 probe. The exon was found to be contained within a fragment of approximately 4 kb.

---

The invention claimed is:

1. A substantially pure polynucleotide, encoding an amino acid sequence selected from the group consisting of SEQ ID NO: 2 and SEQ ID NO: 3.

2. The polynucleotide according to claim 1, comprising SEQ ID NO: 1.

3. A recombinant expression vector comprising a polynucleotide according to claim 1.

4. A recombinant expression vector comprising a polynucleotide according to claim 2.

5. A cell line transformed with a polynucleotide according to claim 1.

6. A cell line transformed with a polynucleotide according to claim 2.

7. A cell line according to claims 5 or 6, wherein the cell line is of mammalian origin.

* * * * *